United States Patent
Correa et al.

(10) Patent No.: US 6,579,698 B1
(45) Date of Patent: Jun. 17, 2003

(54) STABILIZED PROTEINACEOUS PROTEASE INHIBITORS AND VARIANTS THEREOF

(75) Inventors: Paul E. Correa, Cincinnati, OH (US); Charles Winston Saunders, Fairfield, OH (US); Michael Laskowski, Jr., West Lafayette, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/269,262
(22) PCT Filed: Sep. 23, 1997
(86) PCT No.: PCT/US97/16355
§ 371 (c)(1),
(2), (4) Date: Jul. 13, 1999
(87) PCT Pub. No.: WO98/13387
PCT Pub. Date: Apr. 2, 1998

Related U.S. Application Data
(60) Provisional application No. 60/026,944, filed on Sep. 24, 1996.

(51) Int. Cl.⁷ .............................................. C12B 21/06
(52) U.S. Cl. .............. 435/69.1; 435/252.3; 435/252.31; 435/252.33; 435/320.1; 536/23.1; 530/350; 510/108
(58) Field of Search ................. 530/350; 536/23.1; 435/252.3, 252.31, 320.1, 69.1, 219, 183, 252.33; 510/108

(56) References Cited

U.S. PATENT DOCUMENTS

| | | | |
|---|---|---|---|
| 4,636,489 A | 1/1987 | Seemüller et al. | 514/12 |
| 4,760,130 A | 7/1988 | Thompson et al. | 530/350 |
| 4,801,537 A | 1/1989 | Nagarajan et al. | 435/68 |
| 5,039,446 A | 8/1991 | Estell | 252/174.12 |
| 5,079,229 A | 1/1992 | Grütter et al. | 514/12 |
| 5,178,789 A | 1/1993 | Estell | 252/174.12 |
| 5,180,667 A | 1/1993 | Grütter et al. | 435/69.2 |
| 5,527,487 A | 6/1996 | Mikkelsen et al. | 252/174.12 |
| 5,550,042 A | 8/1996 | Sambrook et al. | 435/172.1 |
| 5,616,485 A | 4/1997 | Hadary et al. | 435/220 |
| 5,623,059 A | 4/1997 | Joergensen et al. | 530/412 |
| 5,674,833 A | 10/1997 | Mikkelsen et al. | 510/530 |

FOREIGN PATENT DOCUMENTS

| | | |
|---|---|---|
| CA | 1297437 | 3/1992 |
| EP | 0 352 387 | 1/1990 |
| JP | 03-099099 | 4/1991 |
| JP | 08-038191 | 2/1996 |
| WO | WO 87/04187 | 7/1987 |
| WO | WO 90/02175 | 3/1990 |
| WO | WO 92/03529 | 3/1992 |
| WO | WO 92/05239 | 4/1992 |
| WO | WO 93/13125 | 7/1993 |
| WO | WO 93/17086 | 9/1993 |
| WO | WO 93/20175 | 10/1993 |
| WO | WO 95/02055 | 1/1995 |
| WO | WO 97/15670 | 5/1997 |

OTHER PUBLICATIONS

Mitsui et al. "Crystal structures of *Streptomyces subtilisin* inhibitor and its complex with subtilisin BPN'" Nature 277, 447452, Feb. 1979.*

*Amino Acid Sequence of an Alkaline Proteinase Inhibitor (Streptomyces Subtilisin Inhibtor) from Streptomyces albogriseolus S–3253*, Tokuji Ikenaka, Shoji Odani, Mineko Sakai, Yoko Nabeshima, Sakae Sato, Sawao Murao J. Biochem., 76, 1191–1209 (1974).

*Primary Structure and Inhibitory Properties of a Proteinase Inhibitor Produced by Streptomyces Cacaoi*, Shuichi Kojima Mahito Terabe, Seiichi Taguchi, Haruo Momose, Kin–ichiro Miura Biochimica et Biophysica Acta 1207 (1994) 120–125.

*Inhibition of Subtilisin BPN' by Reaction Site P1 Mutants of Streptomyces Subtilisin Inhibitor*, Shuichi Kojima, Yoshitake Nishiyama, Izumi Kumagai, Kin–ichiro Miura J. Biochem., 109, 377–382 (1991).

*Protein Inhibitors of Proteinases*, Michael Laskowski, Jr., and Ikunoshin Kato Ann. Rev. Biochem. 1980. 49:593–626.

*The Effects of Synthetic Protease Inhibitors on Human Proinsulin Production By Recombinant Bacillus Subtilis Strain*, A.A. Novikov, E.V. Parfenova, D.G. Popov, V.E. Sterkin, A.Y. Strongin Biotechnology Letters vol. 12 No. 8 547–550 (1990).

*Molecular Cloning and Necleotide Sequence Determination of Gene Encoding Streptomyces Subtilisin Inhibitor (SSI)*, Shusei Obata, Seiichi Taguchi, Izumi Kumagai, Kin–ichiro Miura J. Boichem., 105, 367–371 (1989).

*Two Novel Streptomyces Protein Protease Inhibitors*, James E. Strickler, Thomas R. Berka, Joselina Gorniak, James Fornwald, Robert Keys, James J. Rowland, Martin Rosenberg, Dean P. Taylor The Journal of Biological Chemistry vol. 267, No. 5, Issue of Feb. 15, pp. 3236–3241, 1992.

*Plasminostreptin, a Protein Proteinase Inhibitor Produced by Streptomyces antifibrinolyticus*, Hiromu Sugino and Atsushi Kakinuma The Journal of Biological Chemistry vol. 253, No. 5, Issue of Mar. 10, pp. 1546–1555, 1978.

*Partial Amino Acid Sequence of an Alkaline Protease Inhibitor, API–2 (b and c)*, Keitarou Suzuki, Masaru Uyeda, Motoo Shibata Agric. Biol. Chem., 45(3), 629–634, 1981.

(List continued on next page.)

Primary Examiner—Nashaat T. Nashed
(74) Attorney, Agent, or Firm—Kelly McDowDunham; Leonard W. Lewis; Steven W. Miller

(57) ABSTRACT

Protein protease inhibitors and their variants have increased stability in detergent composition. The genes encoding such variants are provided. The variants are used in cleaning compositions.

24 Claims, No Drawings

OTHER PUBLICATIONS

*Streptomyces Subtilisin Inhibito–Like Proteins ARe Distributed Widely in Streptomycetes*, Seiichi Taguchi, Hideki Kikuchi, Masayuki Suzuki, Shuichi Kojima, Mahito Terabe, Kin–ichiro Miura, Takashi Nakase, Haruo Momose Applied and Environmental Microbiology, Dec. 1993, p. 4338–4341.

*High Frequency of SSI–Like Protease Inhibitors among Streptomyces*, Seiichi Taguchi, Hideki Kikuchi, Shuichi Kojima, Izumi Kumagai, Takashi Nakase, Kin–ichiro Miura, Haruo Momose Biosci. Biotech. Biochem., 57(3) 522–524, 1993.

*Comparative Studies on the Primary Structures and Inhibitory Properties of Subtilisin–Trypsin Inhibitors From Streptomyces*, Seiichi Taguch, Shuichi Kojima, Mahito Terabe, Kin–ichiro Miura, Haruo Momose Eur. J. Biochem. 220, 911–918 (1994).

*Mechanisms of Temporary Inhibition in Streptomyces Subtilisin Inhibitor Induced by an Amino Acid Substituion, Tryptophan 86 Replaced by Histidine*, Atsuo Tamura, Kenji Kanaori, Shuichi Kojima, Izumi Kurmgai, Kin–ichiro Miura, Kazuyuki Akasaka Biochemistry 1991, 30, 5275–5286.

*Effect of an Intersubunit Disulfide Bond on the Stability of Streptomyces Subtilisin Inhibitor*, Atsuo Tamura, Shuichi Kojima, Kin–ichiro Miura, Julian M. Sturtevant Boichemistry 1994, 33, 14512–14520.

*Primary Structure and Reactive Site of Streptoverticillium Anticoagulant(SAC), a Novel Protein Inhibitor of Blood Coagulation Produced by Streptoverticillium cinnamoneum subsp. Cinnamoneum*, Masataka Tanabe, Kenji Kawahara, Tsuneo Asano, Koichi Kato, Atsushi Kakinuma J. Boichem. 115, 752–761 (1994).

*A Protease Inhibitor Produced by Streptomyces lividans 66 Exhibits Inhibitory Activities Toward Both Subtilisin BPN' and Trypsin*, Yoshitaka Ueda, Shuichi Kojima, Kouhei Tsumoto, Shigeki Takeda, Kin–ichiro Miura, Izumi Kumangai J. Boichem. 112, 204–211 (1992).

*Three Novel Subtilisin–Trypsin Inhibitors fromStreptomyces: Primary Structures and Inhibitory Properties*, Mahito Terabe, Shuichi Kojima, Seiichi Taguchi, Haruo Momose, Kin–ichiro Miura J. Biochem. 116, 1156–1163 (1994).

* cited by examiner

STABILIZED PROTEINACEOUS PROTEASE INHIBITORS AND VARIANTS THEREOF

CROSS REFERENCE

This application claims priority under Title 35, United States Code 119(e) from Provisional Application Ser. No. 60/026,944, filed Sep. 24, 1996.

TECHNICAL FIELD

This invention relates to protein or proteinaceous protease inhibitors and to novel variants thereof, useful in conjunction with enzymes in cleaning compositions. The invention provides inhibitor variants greater proteolytic stability in detergent. The present invention also relates a variety of cleaning compositions comprising these inhibitors, and the genes encoding them.

BACKGROUND

Enzymes make up the largest class of naturally occurring proteins. Cleaning compositions may include many different enzymes to accomplish stain removal. For example, a liquid laundry detergent may contain proteases, lipases, amylases, peroxidases, and cellulases. The protease's ability to hydrolyze proteins has been exploited in cleaning compositions by incorporating proteases as an additive to aid in removing peptide or protein stains.

However, a commonly encountered problem in such protease-containing liquid aqueous detergents is the degradation by protease of the protease itself or of other enzymes (such as, lipase, amylase and cellulase) in the composition during storage. As a result of this degradation, the detergent composition consequently performs less well. Therefore it is commercially useful to incorporate into the cleaning composition a protease inhibitor.

There is a need to provide inhibitors that are stable enough to be useful. This "usefulness" is measured in terms of the need to provide a long shelf life for the cleaning composition, and an improved yield of the protease from the biological host.

Additionally, these inhibitors could be useful for cleaning compositions, regardless of the composition type, e.g., liquid, gel, granular, or solid compositions.

It would be advantageous to provide reversible inhibitors of the protease, so that upon dilution of the composition during cleaning, or in the cleaning environment, the protease is no longer inhibited, but rather is able to hydrolyze the peptide stains.

Synthetic Protease Inhibitors

Various synthetic protease inhibitors or stabilizers have been proposed for such uses. Panandiker et al. (U.S. Pat. No. 5,422,030) discloses an aromatic borate ester to stabilize enzymes in laundry detergents. For instance, U.S. Pat. No. 4,566,985 proposes to use benzamidine hydrochloride, EP 376 705 proposes to use lower aliphatic alcohols or carboxylic acids, EP 381 262 proposes to use a mixture of a polyol and a boron compound. Such synthetic approaches to enzyme inhibition may provide longer shelf life, but may be expensive and may not improve isolation yield due to proteolysis in the fermentor.

Recognizing these shortcomings, those in the art have experimented with proteinaceous protease inhibitors in hopes of stabilizing enzymes in cleaning compositions, without the drawbacks of the synthetic inhibitors.

Proteinaceous Protease Inhibitors

Nature provides proteinaceous protease inhibitors to regulate the protease in its natural environment (i.e., in vivo). However, these proteinaceous protease inhibitors tend to be unstable, therefore, their commercial use in the presence of proteases and detergents may be somewhat limited.

Proteinaceous protease inhibitors are typically long peptides (often over 28 amino acids), which bind to the active site of a protease and inhibit its activity. These inhibitors have been classified into several families (Families I to IX) based on primary amino acid sequence homologies (Laskowski, M., Jr., and I. Kato, "Protein Inhibitors of Proteinases", *Ann. Rev. Biochemistry*, (1980) 49: 593–626). Included in these inhibitors are those commonly referred to as family VI inhibitors, such inhibitors include eglin and barley chymotrypsin inhibitor, and family III inhibitors, such as Streptomyces subtilisin inhibitor (SSI), and plasminostreptin.

Such inhibitors tend to bind to specific proteases better than others. Thus it is convenient to consider the inhibitor with a specific protease in mind. For this reason, the art often discusses them as "protease/peptide inhibitor pairs." An example of a known protease/peptide inhibitor pair is subtilisin BPN'/SSI. See for example, Y. Mitsui, Y. et al, "Crystal Structure of a Bacterial Protein Proteinase Inhibitor (Streptomyces Subtilisin Inhibitor) at 2.6 A Resolution", *J. Mol. Biol.* 131: 697–724, (1979) and S. Hirono, H. Akagawa, Y. Mitsui, and Y. Iitaka, "Crystal Structure at 1.6 A Resolution of the Complex of Subtilisin BPN' with Streptomyces Subtilisin Inhibitor", *J. Mol. Biol.* 178: 389–413, (1984). Mikkelsen (published application WO 92/03529) discloses peptide inhibitors of family VI. It is said that these inhibitors stabilize lipase and cellulase to proteolysis. Mikkelsen recognizes that many natural inhibitors have a high affinity for the protease and that the inhibitor-enzyme complex does not dissociate upon dilution into the wash environment. Mikkelsen discloses the use of proline in the Family VI P1 position. It is recognized that if the protease is completely inhibited in the product, then only a small fraction of the protease would be active even after dilution in the cleaning environment.

SSI is stable in the presence of subtilisin BPN', as long as the inhibitor is present in sufficient amounts to inhibit all protease activity. However, SSI is unstable in the presence of excess protease.

Tamura et al, (*Biochemistry* 30: 5275–5286, 1991) suggests that SSI's instability in the presence of excess protease is due to dissociation and conformational change of hydrophobically formed SSI dimers. Tamura discloses a D83C variant of SSI displaying a higher $T_m$ than native SSI using DSC (Tamura et al., *Biochemistry* 33:14512–14520, 1994), but Tamura apparently did not test protease resistance in the presence or absence of detergent.

However, if the binding constant (Ki) of an inhibitor provides for some protease activity in the cleaning composition containing the enzyme/inhibitor pair, the protein inhibitor, as well as enzymes in the composition, may be hydrolyzed. Therefore, it would be advantageous to find variants of SSI or other inhibitors which are suitably stable in the presence of protease as well as detergents. In addition, it is preferred that these inhibitors have a binding constant for the particular protease to be inhibited. This binding constant (Ki) should allow for inhibition of the protease in the cleaning composition and during its storage. However, upon diluting the cleaning composition or during the cleaning process, the protease and inhibitor dissociate, and the uninhibited protease becomes active.

The binding of some protease inhibitors has been investigated. Halkier et al. (WO 93/20175) discloses protease inhibitors (e.g., eglin and barley chymotrypsin inhibitors)

with lowered affinity compared to naturally occurring family VI inhibitors, due to changes at the P1 and P4 to P2 positions of the inhibitor.

Since the amino acid sequence of any protein or peptide determines its characteristics, a change in the amino acid sequence may alter the protein's or peptide's properties depending upon the location and nature of the amino acid change. Thus mutagenesis has been employed on some protein protease inhibitors in an attempt to determine the structure or function of certain amino acids therein.

For example, Kojima et al. (S. Kojima, Y. Nishiyama, I. Kumagai, and K. Miura, *J. Biochem.* 109: 377–382, 1991) made and measured the Ki of 19 SSI P1 position variants against wild-type SSI using subtilisin BPN'. As another example, Mikkelsen discloses mutations in family VI inhibitors that are said to lower binding affinity. Nielsen et al. (WO 93/17086) discloses changes to plasminostreptin that are said to lower binding affinity.

The art describes the need for proteinaceous protease inhibitors that are useful. For example, Feder and Kochavi (FR208475 1) disclose a reversible alkaline protease inhibitor which is said to stabilize an enzyme in the presence of detergents. Estell (U.S. Pat. No. 5,178,789) discloses the use of turkey ovomucoid as a reversible inhibitor said to be useful for stabilizing subtilisin.

Of course, for cost reasons and the like, it would be advantageous to provide inhibitors useful at very low levels in cleaning compositions. In addition to this advantage, such an inhibitor would allow for the use of enzymes which are highly sensitive to proteolytic degradation in compositions comprising a protease.

Despite the work in this area, it remains that protein protease inhibitors are generally too unstable in the presence of protease and detergents to be commercially useful.

Despite the variety of approaches described in the art, there is a continuing need for new, and more effective variants of proteases useful for cleaning compositions.

For example, if used in a laundry application, it would be desirable that any inhibitor dissociate from the protease upon dilution in the washing machine, enabling the protease to be active. Because the dilution in a washing machine is finite, the art recognizes that the inhibitor need not render the protease completely inactive in the product, but should render the protease active in the cleaning environment. It would be advantageous to have about 0.01% to about 1% of the protease be free from inhibitor in a composition. If the inhibitor is used in a liquid cleaning composition, those in the art desire inhibitors which are stable in the presence of free protease.

OBJECTS OF THE PRESENT INVENTION

It is an object of the present invention to provide peptide or proteinaceous protease inhibitor variants having greater proteolytic stability, especially in detergent, and lower affinity for the protease than the wild-type inhibitor.

It is also an object of the present invention to provide cleaning compositions comprising these variants.

SUMMARY

The present invention provides peptide or proteinaceous protease inhibitor variants having a modified amino acid sequence from wild-type amino acid inhibitors; wherein the modification positions provides greater proteolytic stability and lower affinity for the protease. The present invention also provides the genes encoding such variants.

The present invention also provides compositions comprising such variants for cleaning.

Other benefits that the invention provides will be apparent as the description of the invention proceeds.

DESCRIPTION

We have found variants of the protease inhibitors which are more stable to free (i.e., uninhibited) protease in vitro and in the presence of surfactants, including detergents. In addition, it is contemplated that such variants are more stable in vivo as well.

We have also found protease inhibitors with suitable inhibition constants (Ki), that provide for suitable inhibition of protease during growth, harvesting, purification and in the cleaning composition. This provides for better stability and longer shelf life (i.e., storage time that the product remains substantially unchanged in its properties.) It is contemplated that better stability results in decreased autolysis and thus increases yield of protease from the organism.

The preferred compositions of the invention comprise three essential ingredients: (A) protein protease inhibitor(s) or a mixture thereof, (B) protease(s) or a mixture thereof, and (C) a surfactant. The compositions according to the present invention may further comprise optional ingredients, including other enzymes.

I. Protease Inhibitors (i.e., Variants)

The term "protease inhibitor", as used herein, means any reversible inhibitor of the proteolytic activity of the protease enzyme. This inhibitor is a protein or polypeptide. Typically, the inhibitor is long enough to be called a protein in its own right, this means that the polypeptide is at least 25 amino acids in length, more preferably at least 28 amino acids, most preferably at least 80 amino acids in length.

Preferably the inhibitor moiety is resistant to proteolysis by the corresponding protease.

This invention pertains to peptide protease inhibitor variants, that have been modified by mutating the various nucleotide sequences that code for the inhibitor, thereby modifying the amino acid sequence of the inhibitor. The modified peptide protease inhibitor variants (hereinafter, "variants") of the present invention have improved stability to proteases, and inhibit protease in the formulation, but dissociate upon dilution (i.e., they "dilute off") in the cleaning environment.

The present invention also pertains to the genes encoding for such variants.

Preferred embodiments of this invention are useful for many proteases for which SSI is an inhibitor. These include, but are not limited to, Savinase, subtilisin BPN', subtilisin Carlsberg, and their derivatives.

Without being bound to any theory, this dissociation upon dilution may be improved by modifying the amino acid sequence to provide variants which have protease binding constants (Ki) which differ from the wild-type proteinaceous protease inhibitors. This improved Ki allows for dissociation in the cleaning process or upon dilution.

The total protease is the sum of inhibitor-bound protease, substrate-bound protease, and free protease. When an inhibitor has the optimal Ki, it provides nearly complete inhibition at the concentration typical in the stored cleaning composition (i.e., on the shelf) and nearly complete dissociation (i.e., lack of inhibition) at the concentration typical in use (e.g., in the washer, in a solution for soaking, etc.). Thus the protease/inhibitor must be diluted to provide active protease.

Preferred variants of the invention are designed to alter the inhibition of the proteases to provide these desirable properties. Preferably this alteration allows the inhibitor to inhibit the protease in the stored product and dissociate upon dilution. These binding affinities, or inhibition constants (Ki) are tailored using site-directed mutagenesis. Furthermore, the affinity of the inhibitor for the protease is optimized for each different protease, and each cleaning application.

In terms of a Ki, a "suitable Ki", "advantageous Ki, desirable Ki, or optimal Ki", as referred to herein, allows the inhibitor to inhibit nearly all protease (preferably above 60%, more preferably about 99%) in the cleaning composition or product, but still allows the inhibitor to dissociate from the protease upon dilution.

For example, where a 1:1 stoichiometry is used, it is preferred that inhibitors have a Ki value between $10^{-10}$ and $10^{-4}$, depending on the application. As another example, a liquid laundry composition, as commonly used in the U.S., preferably has an inhibitor with a Ki between $10^{-10}$ and $10^{-6}$, assuming the composition is diluted 600-fold in the washing machine. Of course, should washing machine dimensions or product concentrations change, the Ki is adjusted accordingly. Prediction of a useful Ki range is readily determined by the skilled artisan without undue experimentation by considering such parameters as dilution of the cleaning formula upon use, temperature dependence of the binding constant in relation to the temperature of cleaning method used, stoichiometry of the inhibitor to the protease, and the like.

In a preferred embodiment, the preferred stoichiometry is 1:1 to about 3:1 (inhibitor:protease), preferably 1.5:1 to about 3:1 (inhibitor:protease), more preferably about 2:1 (inhibitor:protease). In this context, the "suitable Ki" as referred to herein, allows the inhibitor to inhibit nearly all protease (preferably about 99%) in the cleaning composition or product, but still allows the inhibitor to dissociate from the protease upon dilution. Because of the change in stoichiometry, however, it is preferred that inhibitors have a Ki value between $10^{-10}$ and $10^{-4}$, depending on the application. As an example, a liquid laundry composition, used in the U.S., preferably has an inhibitor with a Ki between $10^{-10}$ and $10^{-6}$, assuming the composition is diluted 600-fold in the washing machine, as above. Of course, should washing machine dimensions, product concentrations, or temperature of the wash solution change, the Ki is adjusted accordingly.

Thus the amount of inhibitor used in a cleaning composition is defined by the amount of the protease to be inhibited in the cleaning composition.

As used herein, "variant" means an inhibitor having an amino acid sequence which differs from that of the known wild-type, this variation may be by substitution of one or more amino acids, or by deletion or addition of amino acids either at the ends or in the sequence of the variant. Thus the term "variant" includes "inhibitor like" peptides that have additional amino acids, even if the variant sequence contains the entire wild type sequence.

As used herein, "gene", "vector", "plasmid", "genome", or "chromosome" have their art recognized meanings. However, the skilled artisan will recognize that teaching how to use an expression system using a plasmid, etc. is sufficient to teach the skilled artisan how to use other systems whether they be genomic, plasmid-based, etc., whether they are used in procaryotes or eucaryotes, and whether the heterologous host is bacterial, fungus, plant, etc.

Since the peptide is ultimately encoded in vivo by DNA, the DNA can be used to define the inhibitor sequences. The DNA, which codes for the inhibitor or its variants, can be used in any number of plasmids and/or expression systems, including in vitro expression systems and in vivo systems such as plants, (preferably those used in biotechnology, including tobacco, oilseed plants, such as rapeseed, soybean and the like, grain, such as maize, barley, oats, other vegetables, such as tomatoes, potatoes and the like) and microorganisms, including fungi, such as yeast, and bacteria, such as Bacillus, *E. coli* and the like. Preferably the expression system is a microorganism, more preferably bacterial in nature, most preferably *E. coli* or Bacillus, still more preferably Bacillus.

It is understood that the skilled artisan, given the instruction of this application, will appreciate that the DNA used to code for the inhibitor or its variants, may be placed in the same plasmid, phage or chromosome as other inhibitors of the invention. In addition, such plasmids, phages or chromosomes may also encode proteases, including fusion proteins which include as part of the fusion protein an inhibitor and/or protease, which may or may not be inhibited by the inhibitor of the invention.

The DNA encoding the inhibitor or its variant may be incorporated into a plasmid, or phage, active in the cell, or may be incorporated directly into the genome of the organism which is used in cloning or expression of the inhibitor of the invention.

It is also well understood by the skilled artisan that the DNA described above also contemplates, and discloses the RNA transcript of the DNA. The skilled artisan can, without experimentation, know the RNA sequence, by inspection of the DNA sequence.

As used herein, "mutant gene" means a gene coding for a variant.

As used herein, "wild-type inhibitor" refers to known and naturally derived protease inhibitors. An example of one of these inhibitors is Streptomyces Subtilisin Inhibitor (SSI). SSI is 113 amino acids in length and is described by Obata et al. ("Molecular Cloning and Nucleotide Sequence Determination of Gene Encoding Streptomyces Subtilisin Inhibitor (SSI)", S. Obata, S. Taguchi, I. Kumagai, and K. Miura, *J. Biochem.* 105: 367–371 (1989), incorporated herein by reference. SEQ ID NO:19 shows the wild-type SSI gene of Obata et al. As used herein, the amino acid numbering is that of Obata et al. As used herein, this amino acid numbering is applied to other subtilisin inhibitors from Streptomyces, in accordance with Terabe et al. (infra).

We use a synthetic SSI gene, designed to be rich in adenine and thymine, as is *B. subtilis* DNA. The sequence of the synthetic SSI gene is represented by SEQ ID NO:1. This synthetic gene encodes two extra amino acid residues at the peptide's amino terminus due to expression plasmid construction methods. This modified amino acid sequence, including four additional amino acids, is represented by SEQ ID NO:2. As used herein, the term "wild-type amino acid sequence" and "wild-type inhibitor" is represented by SEQ ID NO:2.

SSI may exist in dimeric form. Thus without being bound by theory, it is possible that stabilizing dimeric SSI provides increased protease resistance to excess protease. Preferably this stabilized dimeric SSI variant is composed of two SSI variant monomers covalently bound together. This may be by ester, amido, disulfide, or other linkages, commonly occurring in amino acids and their sidechains. Thus "covalent dimerization" and "covalent stabilization" refer to such covalently bound monomers, which form the dimer. Preferably this dimerization occurs via disulfide bonds.

For example, we have found that a cysteine at amino acid residue 83 stabilizes SSI. It might also stabilize related inhibitors, such as plasminostreptin, SIL1, SIL2, SIL3, SIL4, STI2, API-2c', SLP1, SIL10, SIL13, SIL14 ("Three Novel Subtilisin-Trypsin Inhibitors from Streptomyces: Primary Structures and Inhibitory Properties", M. Terabe, S. Kojima, S. Taguchi, H. Momose, and K. Miura, *J. Biochem.* 116: 1156–1163, 1994) and other homologous inhibitors from Streptomyces.

II. Protease

A second essential ingredient in the present detergent compositions is from about 0.0001% to 1.0%, preferably about 0.0005% to 0.2%, most preferably about 0.002% to 0.1%, weight % of active protease. Mixtures of protease are also included. The protease can be of animal, plant or, preferably, microorganism origin. Preferred for use herein are subtilisin-type proteases. Particularly preferred is bacterial serine protease (or a variant thereof) obtained from *Bacillus subtilis, Bacillus amyloliquefaciens, Bacillus lentus,* and/or *Bacillus licheniformis*.

Of course, the weight percent of protease in the cleaning composition will vary depending on the water content, builder content and the like of the finished composition. For example, it is preferred that in a granular detergent, 0.064 to about 0.64 mg/g of protease in the composition is desirable. The skilled artisan will appreciate that a gel detergent resembles a liquid formulation. Thus weight percent of protease may be adjusted to compensate for the variables above detergent (as well as others understood in the art).

Suitable proteases include Novo Industries A/S Alcalase$^R$ (preferred), Esperase$^R$, Savinase$^R$ (Copenhagen, Denmark), Gist-brocades' Maxatase$^R$, Maxacal$^R$ and Maxapem 15$^R$ (protein engineered Maxacal$^R$) (Delft, Netherlands), and subtilisin BPN and BPN'(preferred), which are commercially available. Preferred proteases are also modified bacterial serine proteases, such as those made by Genencor International, Inc. (San Francisco, Calif.) which are described in European Patent Application Serial Number 87303761.8, filed Apr. 28, 1987 (particularly pages 17, 24 and 98), and which is called herein "Protease B", and 199,404, Venegas, published Oct. 29, 1986, which refers to a modified bacterial serine protease (Genencor International) which is called "Protease A" herein (same as BPN'). Preferred proteases, then, are selected from the group consisting of Alcalase$^R$ (Novo Industries A/S), BPN', Protease A and Protease B (Genencor), and mixtures thereof. Protease B is most preferred.

III. Surfactant

From about 1 to 80, preferably about 5 to 50, most preferably about 10 to 30, weight % of surfactant is the third essential ingredient in the present invention. The surfactant can be selected from the group consisting of anionics, nonionics, cationics, ampholytics, zwitterionics, and mixtures thereof. Although the compositions according to the present invention are preferably used in the context of laundry cleaning, said compositions according to the present invention can be used in other different cleaning applications including hard surface cleaning, or dishwashing. The particular surfactants used can therefore vary widely depending upon the particular end-use envisioned.

The benefits of the present invention are especially pronounced in compositions containing ingredients that are harsh to enzymes such as certain detergency builders and surfactants.

IV. EXAMPLES

The following examples are not meant to limit the claimed invention in any way, but rather provide the skilled artisan with guidance as to how to make and use the invention. Given the guidance of the examples and the other disclosure of the specification herein and the information readily available to those skilled in the art, the skilled artisan is able to make and use the invention. For brevity, exhaustive recitation of the art and art known methodologies and the like are eliminated, as these are well within the purview of the skilled artisan.

Known starting materials are used for these examples. Many of these materials are commercially available. (Cf., Sigma Catalog, Sigma-Aldrich Corp, Chicago, Ill. 1996) For example, *E. coli* CJ236 and JM101 are known strains, pUB110 and pUC19 are known plasmids, and Kunkel method mutagenesis is also well known in the art. (See for example, Molecular Cloning, A Laboratory Manual, Second Edition, J. Sambrook, E. F. Fritsch, and T. Maniatis, Cold Spring Harbor Laboratory Press, 1989.)

Variants may be made by expression systems and by various methods in various hosts. These methods are within the scope of the practice of the skilled artisan in molecular biology, biochemistry or other arts related to biotechnology, as described above.

The skilled artisan will also appreciate that similar alterations are made to homologous inhibitors from Streptomyces, including inhibitors from *S. hygroscopicus, S. virginiae* and others, based on known or published homologies. (C f., M. Terabe, S. Kojima, S. Taguchi, H. Momose, and K. Miura, "Three Novel Subtilisin-Trypsin Inhibitors from Streptomyces: Primary Structures and Inhibitory Properties." *J. Biochem.* 116:1156–1163, 1994.)

Example 1

Construction of the Synthetic SSI Gene

A gene encoding mature SSI is constructed using standard methods, for example PCR. (See for example, *PCR Protocols: A guide to Methods and Applications* Eds., M. A. Innis et al., Academic Press Inc., 1990) Using standard procedures, these oligonucleotides are initially used pair-wise in the PCR;

SEQ ID NO:3 with 6,
SEQ ID NO:4 with 5,
SEQ ID NO:7 with 10, and
SEQ ID NO:8 with 9.

The first and second pairs are then mixed and used in another round of PCR, as are the third and fourth pairs. PCR oligomers are shown below:

SEQ ID NO:3
5' TCC GAC GAA TTC GAT GCT CCT TCT GCA CTT TAT GCA CCT TCA GCA TTA GTT TTA ACA GTT 3'
SEQ ID NO:4
5' CCT GAA AGA GCA GTA ACT CTT ACA TGT GCT CCA GGC CCT TCT GGT ACA CAT CCA GCA GCT 3'
SEQ ID NO:5
5' ACC TCC TAC TGC AGC TAA ATC TGC ACA TGC AGA GCC AGC TGC TGG ATG TGT 3'
SEQ ID NO:6
5' TAC TGC TCT TTC AGG TGC AGC TGT CGT AGC GCT AAC TCC TTT ACC AAC TGT TAA AAC TAA 3'
SEQ ID NO:7
5' GAT TTA GCT GCA GTA GGA GGT GAC TTA AAC GCA TTA ACA CGT GGT GAA GAC GTT ATG TGT 3'
SEQ ID NO:8
5' GTT GAT GGA GTT TGG CAA GGT AAA CGC GTA TCT TAT GAA CGT GTA TTT TCA AAT GAA TGT 3'

SEQ ID NO:9
5' TGT CCA AAG CTT GGA TCC TTA AAA TGC AAA TAC AGA AGA GCC ATG AGC GTT CAT TTC ACA TTC ATT TGA AAA 3'
SEQ ID NO: 10
5' CCA AAC TCC ATC AAC AGT CAG TAA TAC AGG ATC ATA AAC CAT TGG ACA CAT AAC GTC TTC 3'.

The oligonucleotides are used pairwise in four different PCRs:
SEQ ID NO: 3 with SEQ ID NO: 6,
SEQ ID NO: 4 with SEQ ID NO: 5,
SEQ ID NO: 7 with SEQ ID NO: 10, and
SEQ ID NO: 8 with SEQ ID NO: 9.

10.6 μl of each of the first two PCR products are mixed and used in a 100 μl PCR. To obtain a sufficient quantity of DNA, eight of these PCR tubes are prepared. The PCR products of the third and fourth PCRs are similarly treated. The PCR products are treated with proteinase K, extracted with phenol/chloroform, and precipitated using ethanol.

The product of SEQ ID NO: 3 and 6 is digested with EcoRI and PstI, and the product of SEQ ID NO:7 and 10 is digested with PstI and HindIII. Following phenol/chloroform extraction and ethanol precipitation, these DNAs are ligated to pUC 19 DNA which had been digested with the same restriction enzymes. The ligation mix is used to transform E. coli TG1, selecting on ampicillin plates containing XGAL and IPTG.

White colonies are cultured for DNA preparations. The DNA is characterized by restriction analysis and DNA sequencing. Plasmid pPG1364 contains the synthetic SSI partial gene encoded by oligonucleotides SEQ ID NO: 3 and 6. Plasmid pPG1366 contains the SSI partial gene encoded by oligonucleotides SEQ ID NO: 7 and 10.

To construct a complete synthetic gene encoding mature SSI, pPG1364 is digested with EcoRI, BglI, and PstI. pPG1366 is digested with EcoRI, PstI, and XbaI. The DNAs are ligated. Plasmid pPG1371 contains the assembled synthetic SSI gene, and comprises the large PstI EcoRI fragment of pPG1366 and the small EcoRI PstI fragment of pPG1364. pPG1371 is used for subsequent work.

Construction of the Expression Plasmid

The expression plasmid is derived from pPG580, which is a derivative of plasmids used for production of a 34 amino acid residue fragment of human parathyroid hormone (Optimization of the signal-sequence cleavage site for secretion from Bacillus subtilis of a 34-amino acid fragment of human parathyroid hormone, Saunders et al., Gene 102:277–282 (1991). pPG580 is made of four parts.

First, pPG580 contains a Bacillus amyloliquefaciens subtilisin gene, flanked by HindIII sites, made using PCR with the following oligonucleotides.
SEQ ID NO:11
5' AGA TCC AAG CTT TTC CGC AAT TAT ATC ATT 3'
and
SEQ ID NO:12
5' GGA TTC AAG CTT TGC TCA GTT TTG CTT CTG 3'.
pPG580 contains all but the first base pair of the subtilisin gene sequence as shown by Vasantha et al. ("Genes for alkaline protease and neutral protease from Bacillus amyloliquefaciens contain a large open reading frame between the regions coding for signal sequence and mature protein", J. Bacteriology 159:811–819, 1984).

Second, adjacent to the 3' end of the subtilisin gene is a fragment of (i.e., the beginning of) pBS+ (commercially available from Stratagene, La Jolla, Calif.), which extends about 3.2 kbp from the HindIII site to the pBS+ XbaI site.

Third, adjacent to this XbaI site, a large fragment of pUB110 is inserted. ("The nucleotide sequence of pUB110: some salient features in relation to replication and its regulation", McKenzie et al., Plasmid 15: 93–103, 1986). This fragment extends 4.2 kbp from the pUB110 XbaI site, to its BamHI site. The 324 bp fragment of pUB110 from the BamHI site back to the XbaI site, is thus not present in pPG580.

Fourth, the BamHI site of pUB110 is no longer intact, but is fused to the BglII site of the 32 bp synthetic sequence described by Saunders et al ("Optimization of the signal-sequence cleavage site for secretion from Bacillus subtilis of a 34-amino acid fragment of human parathyroid hormone", Saunders et al., Gene 102:277–282, 1991). This 32 bp sequence is shown below:
SEQ ID NO:13
5' AAG CTT CAG GAT GTT CAT AAT TTT TAA AGA TC 3'

Thus providing the plasmid, pPG580.

pPG580 is modified for further use. The BamHI site and the EcoRI sites are removed by digestion with EcoRI and BamHI. The digest incubation is incubated with T4 DNA polymerase and deoxyribonucleotide triphosphates, in the presence of ligase buffer. The resulting plasmid is hereafter referred to as pPG1301, and lacks BamHI or EcoRI restriction sites, and is used to transform E. coli JM101.

The plasmid is further modified by oligonucleotide-directed mutagenesis to provide an EcoRI site following the signal sequence using the oligonucleotide:
SEQ ID NO:14
5' GCC CAG GCG GCA GGG GAA TTC AAA TCA AAC GGG GAA 3'
and a BamHI site following the translational stop using the oligonucleotide:
SEQ ID NO:15
5' GCG GCA GCT CAG TAA GGA TCC AAC ATA AAA AAC CGG C 3'.

This plasmid is referred to hereinafter as pPG1315. The mutagenesis is carried out using the Kunkel method (Molecular Cloning, A Laboratory Manual, Second Edition, J. Sambrook, E. F. Fritsch, and T. Maniatis, Cold Spring Harbor Laboratory Press, 1989).

An EcoRI/BamHI fragment of pPG1371, a DNA sequence encoding mature SSI, and an EcoRI/BamHI fragment of PG1315, containing a subtilisin gene, are ligated, and the ligation mix is used to transform competent B. subtilis PG632 (Saunders et al., Gene 102:277–282, 1991). Among the kanamycin-resistant transformants is strain PG1181, harboring this new plasmid, hereafter referred to as pPG1376. This plasmid contains the subtilisin gene regulatory elements (promoter, translational start sequences) for driving the expression of a protein fusion containing the subtilisin signal sequence and SSI. This plasmid also contains a 33 bp deletion within the pBS+ portion, immediately upstream of the HindIII site, and in the 3' non-translated portion of the subtilisin gene, formerly present between the BamHI and HindIII sites.

This plasmid, pPG1376, is used to transform E. coli and provides a template for site-directed mutagenesis to create new SSI variants. When B. subtilis is transformed with this plasmid, preferably for expression of the inhibitor, it is hereafter referred to as PG1181. When E. coli strain CJ236 is transformed with this plasmid, preferably as a template for further mutagenesis, this strain is hereafter referred to as PG1401.

Plasmid pPG1376 encodes the subtilisin signal sequence and SSI plus four intervening amino acid residues. Two of these amino acids are the amino-terminal portion of the subtilisin pro sequence, and two of these amino acids are encoded by the EcoRI site used to fuse the genes. When the subtilisin signal sequence is removed, the resulting SSI has four additional amino acid residues at its amino terminus. This amino acid sequence, including these four additional amino acids, is represented by SEQ ID NO:2.

Creation of SSI Variants

A. M73D Variant (Variant 1)

To create a SSI gene encoding a M73D variant, the following mutagenizing oligonucleotide is used:
SEQ ID NO:16
5' GAA GAC GTT ATG TGT CCG GAT GTT TAT GAT CCT GTA 3';
using standard Kunkel method mutagenesis on pPG1376 derived from PG1401. The plasmid is referred to as pPG1378. When competent *B. subtilis* (PG632 strain) is transformed with this plasmid, preferably for expression of the inhibitor, this new strain is hereafter referred to as PG1183. When *E. coli* strain CJ236 is transformed with this plasmid, preferably as a template for further mutagenesis, this strain is hereafter referred to as PG1410.

B. M73D D83C Variant (Variant 2)

To create a SSI gene encoding a M73D D83C variant, the following mutagenizing oligonucleotide is used:
SEQ ID NO:17
5' GTA TTA CTG ACT GTT TGT GGA GTT TGG CAA GGT AAA CGT GTA TCT TAT GAA CGT 3'
using standard Kunkel method mutagenesis on template DNA (i.e., plasmid pPG1378) from PG1410. The new plasmid is referred to as pPG1524. When competent *B. subtilis* (PG632 strain) is transformed with this plasmid it is hereafter referred to as PG1610.

C. M73P D83C Variant (Variant 3)

The M73P D83C variant of SSI is made from a D83C SSI gene template and the following oligonucleotide:
SEQ ID NO:18
5' GAA GAC GTT ATG TGT CCC CCG GTT TAT GAT CCT GTA 3'
using standard Kunkel method mutagenesis.

The following table summarizes the plasmids and expression systems (e.g., bacteria) described as examples of the invention. The list is not limiting but merely provides guidance to the artisan reading the specification.

TABLE 1

Summary of plasmid and bacteria features from examples

| Plasmid | Plasmid Features | strain/ATCC deposit # | |
|---|---|---|---|
| | | E. coli | B. subtilis |
| pPG580 | subtilisin gene | | |
| pPG1301 | subtilisin gene | | |
| pPG1315 | subtilisin gene with both EcoRI and BamHI sites | | |
| pPG1371 | gene segment encoding mature SSI | | |
| pPG1376 | SSI gene cloned adjacent to signal sequence coding region of the subtilisin gene | PG1401 | PG1181/69955 |
| pPG1378 | SSI M73D gene cloned adjacent to signal coding region of the subtilisin gene | PG1410 | PG1183/69957 |
| pPG1524 | SSI M73D D83C gene cloned adjacent to signal sequence coding region of the subtilisin gene | | PG1610/69956 |

Example 3

Isolation of SSI

PG1181 produces a mature SSI-like protein, hereinafter referred to as SSI. The SSI-like protein sequence is largely identical to the known sequence (Molecular Cloning and Nucleotide Sequence Determination of Gene Encoding Streptomyces Subtilisin Inhibitor (SSI), *J. Biochemistry* (1989) 105: 367–371, S. Obata, S. Taguchi, I. Kumagai, and K. Miura. The protein differs from SSI in that it also contains four amino acid residues at its amino terminus (Ala-Gly-Glu-Phe), an artifact of making the fusion of the SSI gene to the expression vector. These extra four amino acid residues are expected to have no effect.

SSI and SSI variants is prepared as follows. The cells are cultured overnight in 2×YT medium (1.6% tryptone, 1% yeast extract, 0.5% sodium chloride). The cells are pelleted, and the supernatant harvested. To the supernatant HCl is added to give a pH of 4. Insoluble material is pelleted by centrifugation. The supernatant is dialyzed against Tris/Cl pH 7.5 (1 mM). After dialysis the Tris/Cl pH7.5 buffer suspending the protein is then raised to a concentration of 20 mM. An anion exchange (DEAE) chromatography column is then used to purify the SSI. The inhibitor is dialyzed again against Tris/Cl pH 7.5 (1 mM).

Example 4

Physical Characterization of M73D D83C SSI

The molecular mass of M73D D83C SSI is determined by mass spectrometry to be 23716.4. This is within 0.006% of the value expected if the protein were a dimer, consistent with all cysteine residues involved in disulfide bonding. This is confirmed by SDS gel electrophoresis of M73D D83C SSI. In the presence of beta-mercaptoethanol, the M73D D83C has the same electrophoretic mobility as wild type SSI. In the absence of beta-mercaptoethanol, the M73D D83C migrates much more slowly, as expected for a covalently linked dimer.

The mass of SSI and M73D SSI is determined by mass spectrometry to be within experimental error of the predicted monomers.

Example 5

Characterization of Variants

A. SSI inhibits subtilisin BPN' and a Y217L variant of BPN'. SSI is mixed with protease and incubated for fifteen minutes at room temperature in the presence of 0.1 M Tris, pH 8.6, 10 mM $CaCl_2$. Protease activity is then measured using the method of DelMar, E. G., C. Largman, J. W. Brodrick and M. C. Geokas, (*Anal. Biochem.*, Vol. 99, pp. 316–320, (1979). Addition of 10 μl of N-succinyl-Ala-Ala-Pro-Phe-p-nitroanilide begins the reaction. The reaction rate is measured by the increase in absorbance at 410 nm.

B. Because it is desirable to incorporate a peptide protease inhibitor with the protease into laundry products, the stability in the product environment is also tested.

The stability of inhibitor is monitored by measuring protease activity over time. If the inhibitor is stable, the level of protease activity will be constant. However, if an inhibitor is destroyed, the protease activity will rise. In this experiment, inhibitors are mixed with 1.1 nmol of a subtilisin BPN' derivative with a Y217L change. Water is added so that the volumes of all samples are the same. Following about ten minutes for the complex to form, in a liquid detergent composition made according to the following formula:

|  | WT % |
|---|---|
| $C_{14-15}$ alkyl (ethoxy 2.25) sulfonic acid | 18.0 |
| $C_{12-13}$ alkyl ethoxylate (9) | 2.0 |
| $C_{12}$-N-methylglucamide | 5.0 |
| Citric acid | 4.0 |
| Ethanol | 3.5 |
| Monoethanolamine | 2.0 |
| 1,2 Propanediol | 7.0 |
| Sodium Formate | 0.6 |
| Tetraethylene pentamine ethoxylate (16) | 1.18 |
| Soil release Polymer | 0.15 |
| Silicone Suds suppresser | 0.10 |
| Brightener | 0.10 |
| Water, NaOH*** and minors | Balance to 100% |

This composition constitutes ⅓ of the total sample volume. 15 μl of sample is mixed with 975 μl of 0.1 M Tris HCl, pH 8.6, 0.01 M $CaCl_2$. This dilution is incubated for thirty minutes at room temperature. After incubation, substrate is added, and the amount of protease is measured.

Both the M73D and M73D D83C SSI largely inhibit the protein in the assay. Within a few days, increased protease activity is observed in the M73D SSI-containing sample, indicating that the inhibitor is being destroyed. By this method, M73D D83C SSI is much less susceptible to this destruction: Protease activity does not rise in M73D D83C-containing samples for weeks. The rise in protease activity is greatly retarded in the presence of M73D D83C SSI, compared to that seen with M73D SSI and wild type SSI.

Thus, M73D D83C SSI is much more resistant to proteolysis under these conditions than is M73D SSI.

The Ki is determined as follows. The inhibitor and 600 μg/ml succinyl-Ala-Ala-Pro-Phe-p-nitroanilide are mixed in 990 μl of a 50 mM Tris pH 8 solution. The reaction is started by the addition of protease, and the rate is followed over twenty minutes. A constant rate is observed over the last ten to fifteen minutes. This rate, compared to the rate in the absence of inhibitor, is used to calculate the Ki according to the equations of Goldstein (The mechanism of enzyme-inhibitor-substrate reactions, *J. Gen. Physiol*, 27:529–580, 1944). M73P D83C SSI is determined to have a Ki of 3 nM.

Example 6

Other Variants

Variants of the present invention are exemplified in the tables below. In describing the specific mutations, the original amino acid occurring in wild-type is given first, the position number second, and the substituted amino acid third. Thus M73D means that the Methionine (M) which appeared as the seventy third amino acid (position 73) in the native inhibitor is replaced with Aspartic acid (D). These variations may stabilize the inhibitor and/or may optimize its Ki. The numbering corresponds to that commonly used for SSI (Obata et al, supra) and ignores the four additional amino acid residues present at the amino terminus of the SSI "wild type"-like variant and SSI variants described in this patent application.

TABLE 2

Single Mutation Variants

D83C-Variant 1
M73D-Variant 4

TABLE 3

Double Mutation Variants

M73D D83C-Variant 2
M73P D83C-Variant 3
M70Q D83C-Variant 5

TABLE 4

Triple Mutation Variants

M73P D83C S98A-Variant 6
M73P Y75A D83C-Variant 7
M73P D83C S98V-Variant 8
M70Q M73P D83C-Variant 9
M73P V74A D83C-Variant 10
M73P V74F D83C-Variant 11
M70Q D83C S98A-Variant 12
G47D M70Q D83C-Variant 13
G47D D83C S98A-Variant 14
G47D M73P D83C-Variant 15
G47D M73D D83C-Variant 16

TABLE 5

Quadruple Mutation Variants

M70Q M73P V74F D83C-Variant 17
M70Q M73P V74W D83C-Variant 18
M70Q M73P D83C S98A-Variant 19
G47D M73P V74F D83C-Variant 20
G47D M73P V74W D83C-Variant 21
G47D M73P D83C S98A-Variant 22

TABLE 6

Quintuple Mutation Variants

G47D M70Q M73P V74F D83C-Variant 23
G47D M70Q M73P V74W D83C-Variant 24
G47D M73P V74F D83C S98A-Variant 25
G47D M73P V74W D83C S98A-Variant 26

These useful variants provide direction to the skilled artisan who may, using these examples, and the teaching of the art, make other variants tailored to the protease of interest.

For this purpose it is also contemplated that the skilled artisan may desire to prepare antibodies to the inhibitor of the invention. These antibodies may be prepared using known methodologies.

For example, the inhibitors of the invention can be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures, now standard in the art, employing the invention compounds as antigens.

The antisera obtained can be used directly or monoclonal antibodies may be obtained by harvesting the peripheral blood lymphocytes or the spleen of the immunized animal and immortalizing the antibody-producing cells, followed by identifying the suitable antibody producers using standard immunoassay techniques.

The polyclonal or monoclonal preparations are then useful in monitoring expression of the invention, using standard test methodologies. Thus it is also envisioned that a kit maybe prepared using these antibodies for one in the field to use to determine expression levels and the like.

Such antibodies can also be coupled to labels such as scintigraphic labels, e.g., technetium 99 or I-131, or fluorescent labels, using standard coupling methods. The labeled antibodies can also be used in competitive assays, such as kinetic assays used to determine Ki.

V. Cleaning Compositions

In another embodiment of the present invention, an effective amount of one or more of the variants are included in compositions useful for cleaning a variety of surfaces in need of peptide stain removal. Such cleaning compositions include detergent compositions for cleaning hard surfaces, unlimited in form (e.g., liquid, gel, bar and granular formation); detergent compositions for cleaning fabrics, unlimited in form (e.g., granular, liquid, gel and bar formulations); dishwashing compositions (unlimited in form); oral cleaning compositions, unlimited in form (e.g., dentifrice, toothpaste and mouthwash formulations); denture cleaning compositions, unlimited in form (e.g., liquid, tablet); and contact lens cleaning compositions, unlimited in form (e.g., liquid, tablet).

The cleaning compositions also comprise, in addition to the variants described hereinbefore, one or more cleaning composition materials compatible with the protease inhibitor. The term "cleaning composition material", as used herein, means any liquid, solid or gaseous material selected for the particular type of cleaning composition desired and the form of the product (e.g., liquid, granule, bar, spray, stick, paste, gel), which materials are also compatible with the variant used in the composition. The specific selection of cleaning composition materials are readily made by considering the surface material to be cleaned, the desired form of the composition for the cleaning condition during use (e.g., through the wash detergent use).

As used herein, "non-fabric cleaning compositions" include hard surface cleaning compositions, dishwashing compositions, oral cleaning compositions, denture cleaning compositions and contact lens cleaning compositions.

A. Inhibitor Variants

The term "compatible", as used herein, means the cleaning composition materials do not reduce the proteolytic activity of the variant to such an extent that the protease is not effective as desired during normal use situations. Specific cleaning composition materials are exemplified in detail hereinafter.

As used herein, "effective amount of variant" refers to the quantity of variant necessary to achieve the inhibition of the protease in composition, but the enzymatic activity necessary in the specific cleaning composition in the cleaning environment. Such effective amounts are readily ascertained by one of ordinary skill in the art and are based on many factors, such as the particular variant used, the cleaning application, the specific composition of the cleaning composition, and whether a liquid or dry (e.g., granular, bar) composition is required, and the like. Preferably the cleaning compositions comprise from about 0.0001% to about 10% of one or more variants of the present invention, more preferably from about 0.001% to about 1%, more preferably still from about 0.01% to about 0.1%. Several examples of various cleaning compositions wherein the variants may be employed are discussed in further detail below. All parts, percentages and ratios used herein are by weight unless otherwise specified.

The variants of the present invention can be used in a variety of detergent compositions where high sudsing and good insoluble substrate removal are desired. Thus the variants can be used with various conventional ingredients to provide fully-formulated hard-surface cleaners, dishwashing compositions, fabric laundering compositions and the like. Such compositions can be in the form of liquids, granules, bars and the like. Such compositions can be formulated as modem "concentrated" detergents which contain as much as 30%–60% by weight of surfactants.

B. Surfactants

The cleaning compositions herein can optionally, and preferably, contain various anionic, nonionic, zwitterionic, etc., surfactants. Such surfactants are typically present at levels of from about 5% to about 35% of the compositions.

1. Anionic Surfactants

One type of anionic surfactant which can be utilized encompasses alkyl ester sulfonates. These are desirable because they can be made with renewable, non-petroleum resources. Preparation of the alkyl ester sulfonate surfactant component can be effected according to known methods disclosed in the technical literature. For instance, linear esters of $C_8$–$C_{20}$ carboxylic acids can be sulfonated with gaseous $SO_3$ according to *The Journal of the American Oil Chemists Society*, 52 (1975), pp. 323–329. Suitable starting materials would include natural fatty substances as derived from tallow, palm, and coconut oils, etc.

The preferred alkyl ester sulfonate surfactant, especially for laundry applications, comprises alkyl ester sulfonate surfactants. Suitable salts include metal salts such as sodium, potassium, and lithium salts, and substituted or unsubstituted ammonium salts, such as methyl-, dimethyl-, trimethyl-, and quaternary ammonium cations, e.g. tetramethyl-ammonium and dimethyl piperdinium, and cations derived from alkanolamines, e.g. monoethanolamine, diethanolamine, and triethanolamine. Preferably, the surfactant contains $C_{10}$–$C_{16}$ alkyl, and methyl, ethyl or isopropyl. Especially preferred are the methyl ester sulfonates having a $C_{14}$–$C_{16}$ alkyl.

Alkyl sulfate surfactants are another type of anionic surfactant of importance for use herein. In addition to providing excellent overall cleaning ability when used in combination with polyhydroxy fatty acid amides (see below), these surfactants provide good grease/oil cleaning over a wide range of temperatures, wash concentrations, and wash times. These surfactants, and their water soluble salts or acids of the formula $ROSO_3M$; wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g., sodium, potassium, lithium), substituted or unsubstituted ammonium cations such as methyl-, dimethyl-, and trimethyl ammonium and quaternary ammonium cations, e.g., tetramethyl-ammonium and dimethyl piperdinium, and cations derived from alkanolamines such as ethanolamine, diethanolamine, triethanolamine, and mixtures thereof, and the like. Typically, alkyl chains of $C_{12-16}$ are preferred for lower wash temperatures (e.g., below about 50° C.) and $C_{16-18}$ alkyl chains are preferred for higher wash temperatures (e.g., above about 50° C.).

Alkyl alkoxylated sulfate surfactants are another category of useful anionic surfactant. These surfactants are water soluble salts or acids typically of the formula $RO(A)_mSO_3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl-, trimethyl-ammonium and quaternary ammonium cations, such as tetramethyl-ammonium, dimethyl piperidinium and cations derived from alkanolamines, e.g. monoethanolamine, diethanolamine, and triethanolamine, and mixtures thereof. Exemplary surfactants are $C_{12}$–$C_{18}$ alkyl polyethoxylate (1.0) sulfate, $C_{12}$–$C_{18}$ alkyl polyethoxylate (2.25) sulfate, $C_{12}$–$C_{18}$ alkyl polyethoxylate (3.0) sulfate, and $C_{12}$–$C_{18}$ alkyl polyethoxylate (4.0) sulfate wherein M is conveniently selected from sodium and potassium.

Other anionic surfactants useful for cleaning purposes can also be included in the compositions hereof. These can include salts (including, for example, sodium, potassium, ammonium, and substituted ammonium salts such as mono-, di- and triethanolamine salts) of soap, $C_9$–$C_{20}$ linear alkylbenzenesulphonates, $C_8$–$C_{22}$ primary or secondary alkanesulphonates, $C_8$–$C_{24}$ olefinsulphonates, sulphonated polycarboxylic acids prepared by sulphonation of the pyrolyzed product of alkaline earth metal citrates, e.g., as described in British patent specification No. 1,082,179, alkyl glycerol sulfonates, fatty acyl glycerol sulfonates, fatty oleyl glycerol sulfates, alkyl phenol ethylene oxide ether sulfates, paraffin sulfonates, alkyl phosphates, isothionates such as the acyl isothionates, N-acyl taurates, fatty acid amides of methyl tauride, alkyl succinamates and sulfosuccinates, monoesters of sulfosuccinate (especially saturated and unsaturated $C_{12}$–$C_{18}$ monoesters) diesters of sulfosuccinate (especially saturated and unsaturated $C_6$–$C_{14}$ diesters), N-acyl sarcosinates, sulfates of alkylpolysaccharides such as the sulfates of alkylpolyglucoside (the nonionic nonsulfated compounds being described below), branched primary alkyl sulfates, alkyl polyethoxy carboxylates such as those of the formula $RO(CH_2CH_2O)_kCH_2COO$—$M^+$ wherein R is a $C_8$–$C_{22}$ alkyl, k is an integer from 0 to 10, and M is a soluble salt-forming cation, and fatty acids esterified with isethionic acid and neutralized with sodium hydroxide. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch), and a variety of such surfactants are also generally disclosed in U.S. Pat. No. 3,929,678, issued Dec. 30, 1975 to Laughlin, et al. at Column 23, line 58 through Column 29, line 23. (Both references are herein incorporated by reference).

2. Nonionic Detergent Surfactants

Suitable nonionic detergent surfactants are generally disclosed in U.S. Pat. No. 3,929,678, Laughlin et al., issued Dec. 30, 1975, at column 13, line 14 through column 16, line 6, incorporated herein by reference. Exemplary, non-limiting classes of useful nonionic surfactants are listed below.

1. The polyethylene, polypropylene, and polybutylene oxide condensates of alkyl phenols. In general, the polyethylene oxide condensates are preferred. These compounds include the condensation products of alkyl phenols having an alkyl group containing from about 6 to about 12 carbon atoms in either a straight chain or branched chain configuration with the alkylene oxide. In a preferred embodiment, the ethylene oxide is present in an amount equal to from about 5 to about 25 moles of ethylene oxide per mole of alkyl phenol. Commercially available nonionic surfactants of this type include Igepal$^R$ CO-630, marketed by the GAF Corporation; and Triton$^R$ X-45, X-114, X-100, and X-102, all marketed by the Rohm & Haas Company. These compounds are commonly referred to as alkyl phenol alkoxylates, (e.g., alkyl phenol ethoxylates).

2. The condensation products of aliphatic alcohols with from about 1 to about 25 moles of ethylene oxide. The alkyl chain of the aliphatic alcohol can either be straight or branched, primary or secondary, and generally contains from about 8 to about 22 carbon atoms. Particularly preferred are the condensation products of alcohols having an alkyl group containing from about 10 to about 20 carbon atoms with from about 2 to about 18 moles of ethylene oxide per mole of alcohol. Examples of commercially available nonionic surfactants of this type include Tergitol$^R$ 15-S-9 (the condensation product of $C_{11}$–$C_{15}$ linear secondary alcohol with 9 moles ethylene oxide), Tergitol$^R$ 24-L-6 NMW (the condensation product of $C_{12}$–$C_{14}$ primary alcohol with 6 moles ethylene oxide with a narrow molecular weight distribution), both marketed by Union Carbide Corporation; Neodol$^R$ 45-9 (the condensation product of $C_{14}$–$C_{15}$ linear alcohol with 9 moles of ethylene oxide), Neodol$^R$ 23-6.5 (the condensation product of $C_{12}$–$C_{13}$ linear alcohol with 6.5 moles of ethylene oxide), Neodol$^R$ 45-7 (the condensation product of $C_{14}$–$C_{15}$ linear alcohol with 7 moles of ethylene oxide), Neodol$^R$ 45-4 (the condensation product of $C_{14}$–$C_{15}$ linear alcohol with 4 moles of ethylene oxide), marketed by Shell Chemical Company, and Kyro$^R$ EOB (the condensation product of $C_{13}$–$C_{15}$ alcohol with 9 moles ethylene oxide), marketed by The Procter & Gamble Company. This category of nonionic surfactant is referred to generally as "alkyl ethoxylates."

3. The condensation products of ethylene oxide with a hydrophobic base formed by the condensation of propylene oxide with propylene glycol. The hydrophobic portion of these compounds preferably has a molecular weight of from about 1500 to about 1800 and exhibits water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially-available Pluronic$^R$ surfactants, marketed by BASF.

4. The condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic$^R$ compounds, marketed by BASF.

5. Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants, having alkyl, hydroxyalkyl, or alkyl phenyl group or mixtures thereof containing from about 8 to about 26 carbon atoms; hydroxyalkylene group or a polyethylene oxide group containing from about 1 to about 3 ethylene oxide groups. Such groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

6. Alkylpolysaccharides disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

Optionally, and less desirably, there can be a polyalkylene-oxide chain joining the hydrophobic moiety and the polysaccharide moiety. The preferred alkyleneoxide is ethylene oxide. Typical hydrophobic groups include alkyl groups, either saturated or unsaturated, branched or unbranched containing from about 8 to about 18, preferably from about 10 to about 16, carbon atoms. Preferably, the alkyl group is a straight chain saturated alkyl group. The alkyl group can contain up to about 3 hydroxy groups and/or the polyalkyleneoxide chain can contain up to about 10, preferably less than 5, alkyleneoxide moieties. Suitable alkyl polysaccharides are octyl, nonyl, decyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/ or galactoses. Suitable mixtures include coconut alkyl, di-, tri-, tetra-, and pentaglucosides and tallow alkyl tetra-, penta-, and hexa-glucosides.

The preferred alkylpolyglycosides contain a capping group selected from consisting of alkyl, alkyl-phenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

7. Fatty acid amide surfactants preferably having an alkyl group containing from about 7 to about 21 (preferably from about 9 to about 17) carbon atoms. Preferred amides are $C_8$–$C_{20}$ ammonia amides, monoethanolamides, diethanolamides, and isopropanolamides.

3. Cationic Surfactants

Cationic surfactants can also be included in detergent compositions of the present invention. Cationic surfactants include the ammonium surfactants such as alkyldimethylammonium halogenides, and those surfactants having alkyl, alkylaryl, or aryl sidechains; hydroylated or oxygenated sidechains, including polymers of cellulose of other sugars or sugar like moieties, preferably having a molecular weight less than about 1000; and X is any compatible anion.

Other cationic surfactants useful herein are also described in U.S. Pat. No. 4,228,044, Cambre, issued Oct. 14, 1980, incorporated herein by reference.

4. Other Surfactants

Ampholytic surfactants can be incorporated into the detergent compositions hereof. These surfactants can be broadly described as aliphatic derivatives of secondary or tertiary amines, or aliphatic derivatives of heterocyclic secondary and tertiary amines in which the aliphatic radical can be straight chain or branched. One of the aliphatic substituents contains at least about 8 carbon atoms, typically from about 8 to about 18 carbon atoms, and at least one contains an anionic water-solubilizing group, e.g., carboxy, sulfonate, sulfate. See U.S. Pat. No. 3,929,678 to Laughlin et al., issued Dec. 30, 1975 at column 19, lines 18–35 (herein incorporated by reference) for examples of ampholytic surfactants.

Zwitterionic surfactants can also be incorporated into the detergent compositions hereof. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 to Laughlin et al., issued Dec. 30, 1975 at column 19, line 38 through column 22, line 48 (herein incorporated by reference) for examples of zwitterionic surfactants.

Ampholytic and zwitterionic surfactants are generally used in combination with one or more anionic and/or nonionic surfactants.

The liquid detergent compositions hereof may also contain an "enzyme performance-enhancing amount" of polyhydroxy fatty acid amide surfactant. By "enzyme-enhancing" is meant that the formulator of the composition can select an amount of polyhydroxy fatty acid amide to be incorporated into the compositions that will improve enzyme cleaning performance of the detergent composition. In general, for conventional levels of enzyme, the incorporation of about 1%, by weight, polyhydroxy fatty acid amide will enhance enzyme performance.

The detergent compositions hereof will typically comprise at least about 1% weight basis, polyhydroxy fatty acid amide surfactant and preferably at least from about 3% to about 50%, most preferably from about 3% to 30%, of the polyhydroxy fatty acid amide.

The polyhydroxy fatty acid amide surfactant is of formula

 (I)

where $R^1$ is H, $C_1$–$C_4$ hydrocarbyl, 2-hydroxy ethyl, 2-hydroxy propyl, or a mixture thereof, preferably $C_1$–$C_4$ alkyl, more preferably $C_1$ or $C_2$ alkyl, most preferably $C_1$ alkyl (i.e., methyl); and $R^2$ is a $C_5$–$C_{31}$ hydrocarbyl, preferably straight chain $C_7$–$C_{19}$ alkyl or alkenyl, more preferably straight chain $C_9$–$C_7$ alkyl or alkenyl, most preferably straight chain $C_{11}$–$C_{15}$ alkyl or alkenyl, or mixtures thereof; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z preferably will be derived from a reducing sugar in a reductive amination reaction; more preferably Z will be a glycityl. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —$CH_2$—$(CHOH)_n$—$CH_2OH$, —$CH(CH_2OH)$—$(CHOH)_{n-1}$—$CH_2OH$, —$CH_2$—$(CHOH)_2(CHOR')(CHOH)$—$CH_2OH$, and alkoxylated derivatives thereof, where n is an integer from 3 to 5, inclusive, and R' is H or a cyclic or aliphatic monosaccharide. Most preferred are glycosyls wherein n is 4, particularly —$CH_2$—$(CHOH)_4$—$CH_2OH$.

R' can be, for example, N-methyl, N-ethyl, N-propyl, N-isopropyl, N-butyl, N-2-hydroxy ethyl, or N-2-hydroxy propyl.

$R_2$—CO—NR, Z can be, for example, cocamide, stearamide, oleamide, lauramide, myristamide, capricamide, palmitamide, tallowamide, etc.

Z can be 1-deoxyglucosyl, 2-deoxyfructosyl, 1-deoxymaltosyl, 1-deoxylactosyl, 1deoxygalactosyl, 1-deoxymannosyl, 1-deoxymaltotriotosyl, etc.

Methods for making polyhydroxy fatty acid amides are known in the art. In general, they can be made by reacting an alkyl amine with a reducing sugar in a reductive amination reaction to form a corresponding N-alkyl polyhydroxyamine, and then reacting the N-alkyl polyhydroxyamine with a fatty aliphatic ester or triglyceride in a condensation/amidation step to form the N-alkyl, N-polyhydroxy fatty acid amide product. Processes for making compositions containing polyhydroxy fatty acid amides are disclosed, for example, in G.B. Patent Specification 809,060, published Feb. 18, 1959, by Thomas Hedley & Co., Ltd., U.S. Pat. No. 2,965,576, issued Dec. 20, 1960 to E. R. Wilson, and U.S. Pat. No. 2,703,798, Anthony M. Schwartz, issued Mar. 8, 1955, and U.S. Pat. No. 1,985,424, issued Dec. 25, 1934 to Piggott, each of which is incorporated herein by reference.

Nonlimiting examples of surfactants useful herein include the $C_{11}$–$C_{18}$ alkyl benzene sulfonates and primary and random alkyl sulfates, the $C_{10}$–$C_{18}$ secondary (2,3) alkyl sulfates of the formulas $CH_3(CH_2)_x(CHOSO_3)^-M^+)CH_3$ and $CH_3(CH_2)_y(CHOSO_3^-M^+)$ $CH_2CH_3$ wherein x and (y+1) are integers of at least about 7, preferably at least about 9, and M is a water-solubilizing cation, especially sodium, the $C_{10}$–$C_{18}$ alkyl alkoxy sulfates (especially EO 1–5 ethoxy sulfates), $C_{10}$–$C_{18}$ alkyl alkoxy carboxylates (especially the EO 1–5 ethoxycarboxylates), the $C_{10}$–$C_{18}$ alkyl polyglycosides, and their corresponding sulfated polyglycosides, $C_{12}$–$C_{18}$ alpha-sulfonated fatty acid esters, $C_{12}$–$C_{18}$ alkyl and alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like. The alkyl alkoxy sulfates (AES) and alkyl alkoxy carboxylates (AEC) are preferred herein. (Use of such surfactants in combination with the aforesaid amine oxide and/or betaine or sultaine surfactants is also preferred, depending on the desires of the formulator.) Other conventional useful surfactants are listed in standard texts. Particularly useful surfactants include the $C_{10}$–$C_{18}$ N-methyl glucamides disclosed in U.S. Pat. No. 5,194,639, Connor et al., issued Mar. 16, 1993, incorporated herein by reference.

A wide variety of other ingredients useful in detergent cleaning compositions can be included in the compositions herein, including other active ingredients, carriers, hydrotropes, processing aids, dyes or pigments, solvents for liquid formulations, etc. If an additional increment of sudsing is desired, suds boosters such as the $C_{10}$–$C_{16}$ alkolamides can be incorporated into the compositions, typically at about 1% to about 10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, from about 0.1% to about 2%, to provide additional sudsing.

C. Proteases and Other Enzymes

The formulator may wish to employ various additional enzymes, such as cellulases, lipases, amylases and proteases in such compositions, typically at levels of from about 0.001% to about 1% by weight. Various and fabric care enzymes are well-known in the laundry detergent art.

Preferred compositions herein further comprise a performance-enhancing amount of a detergent-compatible second enzyme. By "detergent-compatible" is meant compatibility with the other ingredients of a liquid detergent composition, such as surfactant and detergency builder. These second enzymes are preferably selected from the group consisting of lipase, amylase, cellulase, and mixtures thereof. The term "second enzyme" excludes the proteases discussed above, so each composition contains at least two kinds of enzyme, including at least one protease. The amount of second enzyme used in the composition varies according to the type of enzyme. In general, from about 0.0001 to 0.3, more preferably 0.001 to 0.1, weight % of these second enzymes are preferably used. Mixtures of the same class of enzymes (e.g. lipase) or two or more classes (e.g. cellulase and lipase) may be used. Purified or nonpurified forms of the enzyme may be used.

Any lipolytic enzyme suitable for use in a liquid detergent composition can be used in these compositions. Suitable lipase enzymes for use herein include those of bacterial and fungal origin.

Suitable bacterial lipases include those produced by microorganisms of the Pseudomonas groups, such as *Pseudomonas stutzeri* ATCC 19.154, as disclosed in British Patent 1,372,034, incorporated herein by reference. Suitable lipases include those which show a positive immunological cross-reaction with the antibody of the lipase produced by the microorganism *Pseudomonas fluorescens* IAM 1057. This lipase and a method for its purification have been described in Japanese Patent Application 53-20487, laid open on Feb. 24, 1978. This lipase is available from Amano Pharmaceutical Co. Ltd., Nagoya, Japan, under the trade name Lipase P "Amano," hereinafter referred to as "Amano-P." Such lipases should show a positive immunological cross-reaction with the Amano-P antibody, using the standard and well-known immunodiffusion procedure according to Ouchterlony (*Acta. Med. Scan.*, 133, pages 76–79 (1950)). These lipases, and a method for their immunological cross-reaction with Amano-P, are also described in U.S. Pat. No. 4,707,291, Thom et al., issued Nov. 17, 1987, incorporated herein by reference. Typical examples thereof are the Amano-P lipase, the lipase ex *Pseudomonas fragi* FERM P 1339 (available under the trade name Amano-B), lipase ex *Pseudomonas nitroreducens* var. *lipolyticum* FERM P 1338 (available under the trade name Amano-CES), lipases ex *Chromobacter viscosum*, e.g. *Chromobacter viscosum* var. *lipolyticum* NRRLB 3673, commercially available from Toyo Jozo Co., Tagata, Japan; and further *Chromobacter viscosum* lipases from U.S. Biochemical Corp., U.S.A. and Disoynth Co., The Netherlands, and lipases ex *Pseudomonas gladioli*.

Suitable fungal lipases include those producible by *Humicola lanuginosa* and *Thermomyces lanuginosus*. Most preferred is lipase obtained by cloning the gene from *Humicola lanuginosa* and expressing the gene in *Aspergillus oryzae* as described in European Patent Application 0 258 068 (Novo Industries A/S), commercially available from Novo Nordisk A/S under the trade name Lipolase$^R$.

From about 10 to 18000, preferably about 60 to 6000, lipase units per gram (LU/g) of lipase can be used in these compositions. A lipase unit is that amount of lipase which produces 1 mmol of titratable fatty acid per minute in a pH stat, where pH is 9.0, temperature is 30° C., substrate is an emulsion of 3.3 wt % of olive oil and 3.3% gum arabic, in the presence of 13 mmol/l $Ca^{++}$ and 20 mmol/l NaCl in 5 mmol/l Tris-buffer.

Any cellulase suitable for use in a liquid detergent composition can be used in these compositions. Suitable cellulase enzymes for use herein include those from bacterial and fungal origins. Preferably, they will have a pH optimum of between 5 and 9.5. From about 0.0001 to 0.1 weight % cellulase can be used.

Suitable cellulases are disclosed in U.S. Pat. No. 4,435, 307, Barbesgaard et al., issued Mar. 6, 1984, incorporated herein by reference, which discloses fungal cellulase produced from *Humicola insolens*. Suitable cellulases are also disclosed in GB-A-2.075.028, GB-A-2.095.275 and DE-OS-2.247.832.

Examples of such cellulases are cellulases produced by a strain of *Humicola insolens* (*Humicola grisea* var. *thermoidea*), particularly the Humicola strain DSM 1800, and cellulases produced by a fungus of Bacillus N or a cellulase 212-producing fungus belonging to the genus Aeromonas, and cellulase extracted from the hepatopancreas of a marine mollusk (Dolabella Auricula Solander).

Any amylase suitable for use in a liquid detergent composition can be used in these compositions. Amylases include, for example, amylases obtained from a special strain of *B. licheniformis*, described in more detail in British Patent Specification No. 1,296,839 (Novo). Amylolytic proteins include, for example, Rapidase$^R$, International Bio-Synthetics, Inc. and Termamyl$^R$ Novo Industries.

From about 0.0001% to 0.55, preferably 0.0005 to 0.1, wt. % amylase can be used.

D. Other (Optional) Ingredients

The liquid detergent compositions herein can contain water and other solvents as carriers. Low molecular weight primary or secondary alcohols exemplified by methanol, ethanol, propanol, and isopropanol are suitable. Monohydric alcohols are preferred for solubilizing surfactants, but polyols such as those containing from about 2 to about 6 carbon atoms and from about 2 to about 6 hydroxy groups (e.g., 1,3-propanediol, ethylene glycol, glycerine, and 1,2-propanediol) can also be used. The compositions may contain from about 5% to about 90%, typically from about 10% to about 50% of such carriers.

The detergent compositions herein will preferably be formulated such that during use in aqueous cleaning operations, the wash water will have a pH between about 6.8 and about 11.0. Finished products thus are typically formulated at this range. Techniques for controlling pH at recommended usage levels include the use of buffers, alkalis, acids, etc., and are well known to those skilled in the art.

Various bleaching compounds, such as the percarbonates, perborates and the like, can be used in such compositions, typically at levels from about 1% to about 15% by weight. If desired, such compositions can also contain bleach activators such as tetraacetyl ethylenediamine, nonanoyloxybenzene sulfonate, and the like, which are also known in the art. Usage levels typically range from about 1% to about 10% by weight.

Various soil release agents, especially of the anionic oligoester type, various chelating agents, especially the aminophosphonates and ethylenediaminedisuccinates, various clay soil removal agents, especially ethoxylated tetraethylene pentamine, various dispersing agents, especially polyacrylates and polyasparatates, various brighteners, especially anionic brighteners, various suds suppressors, especially silicones and secondary alcohols, various fabric softeners, especially smectite clays, and the like can all be used in such compositions at levels ranging from about 1% to about 35% by weight. Standard formularies and published patents contain multiple, detailed descriptions of such conventional materials.

Enzyme stabilizers may also be used in the cleaning compositions. Such stabilizers include propylene glycol (preferably from about 1% to about 10%), sodium formate (preferably from about 0.1% to about 1%) and calcium formate (preferably from about 0.1% to about 1%).

When formulating the hard surface cleaning compositions and fabric cleaning compositions of the present invention, the formulator may wish to employ various builders at levels from about 5% to about 50% by weight. Typical builders include the 1–10 micron zeolites, polycarboxylates such as citrate and oxydisuccinates, layered silicates, phosphates, and the like. Other conventional builders are listed in standard formularies.

From 0 to about 50 weight % detergency builder can be used herein. Inorganic as well as organic builders can be used. When present, the compositions will typically comprise at least about 1% builder. Liquid formulations preferably comprise from about 3% to 30%, more preferably about 5 to 20%, by weight, of detergent builder.

Inorganic detergent builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. Borate builders, as well as builders containing borate-forming materials that can produce borate under detergent storage or wash conditions (hereinafter, collectively "borate builders"), can also be used. Preferably, non-borate builders are used in the compositions of the invention intended for use at wash conditions less than about 50° C., especially less than about 40° C.

Examples of silicate builders are the alkali metal silicates, particularly those having a SiO$_2$:Na$_2$O ratio in the range 1.6:1 to 3.2:1 and layered silicates, such as the layered sodium silicates described in U.S. Pat. No. 4,664,839, issued May 12, 1987 to H. P. Rieck, incorporated herein by reference. However, other silicates may also be useful such as for example magnesium silicate, which can serve as a crispening agent in granular formulations, as a stabilizing agent for oxygen bleaches, and as a component of suds control systems.

Examples of carbonate builders are the alkaline earth and alkali metal carbonates, including sodium carbonate and sesquicarbonate and mixtures thereof with ultra-fine calcium carbonate as disclosed in German Patent Application No. 2,321,001 published on Nov. 15, 1973, the disclosure of which is incorporated herein by reference.

Aluminosilicate builders are useful in the present invention. Aluminosilicate builders are of great importance in most currently marketed heavy duty granular detergent compositions, and can also be a significant builder ingredient in liquid detergent formulations. Aluminosilicate builders include those having the empirical formula:

M$_z$(zAlO$_2$.ySiO$_2$)

wherein M is sodium, potassium, ammonium or substituted ammonium, z is from about 0.5 to about 2; and y is 1; this material having a magnesium ion exchange capacity of at least about 50 milligram equivalents of CaCO$_3$ hardness per gram of anhydrous aluminosilicate. Preferred aluminosilicates are zeolite builders which have the formula:

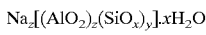

Na$_z$[(AlO$_2$)$_z$(SiO$_x$)$_y$]·xH$_2$O wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al., issued Oct. 12, 1976, incorporated herein by reference. Preferred synthetic crystalline aluminosilicate ion exchange materials useful herein are available under the designations Zeolite A, Zeolite P (B), and Zeolite X. In an especially preferred embodiment, the crystalline aluminosilicate ion exchange material has the formula:

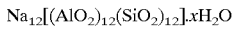

Na$_{12}$[(AlO$_2$)$_{12}$(SiO$_2$)$_{12}$]·xH$_2$O wherein x is from about 20 to about 30, especially about 27. This material is known as Zeolite A. Preferably, the aluminosilicate has a particle size of about 0.1–10 microns in diameter.

Specific examples of polyphosphates are the alkali metal tripolyphosphates, sodium, potassium and ammonium pyrophosphate, sodium and potassium and ammonium pyrophosphate, sodium and potassium orthophosphate, sodium polymeta phosphate in which the degree of polymerization ranges from about 6 to about 21, and salts of phytic acid.

Examples of phosphonate builder salts are the water-soluble salts of ethane 1-hydroxy-1,1-diphosphonate, particularly the sodium and potassium salts, the water-soluble salts of methylene diphosphonic acid e.g. the trisodium and tripotassium salts and the water-soluble salts of substituted methylene diphosphonic acids, such as the trisodium and tripotassium ethylidene, isopyropylidene benzylmethylidene and halo methylidene phosphonates. Phosphonate builder salts of the aforementioned types are disclosed in U.S. Pat. Nos. 3,159,581 and 3,213,030 issued Dec. 1, 1964 and Oct. 19, 1965, to Diehl; U.S. Pat. No. 3,422,021 issued Jan. 14, 1969, to Roy; and U.S. Pat. Nos. 3,400,148 and 3,422,137 issued Sep. 3, 1968, and Jan. 14, 1969 to Quimby, said disclosures being incorporated herein by reference.

Organic detergent builders preferred for the purposes of the present invention include a wide variety of polycarboxylate compounds. As used herein, "polycarboxylate" refers to compounds having a plurality of carboxylate groups, preferably at least 3 carboxylates.

Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates. A number of ether polycarboxylates have been disclosed for use as detergent builders. Examples of useful ether polycarboxylates include oxydisuccinate, as disclosed in Berg, U.S. Pat. No. 3,128,287, issued Apr. 7, 1964, and Lamberti et al., U.S. Pat. No. 3,635,830, issued Jan. 18, 1972, both of which are incorporated herein by reference.

A specific type of ether polycarboxylates useful as builders in the present invention also include those having the general formula:

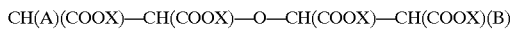

CH(A)(COOX)—CH(COOX)—O—CH(COOX)—CH(COOX)(B)

wherein A is H or OH; B is H or —O—CH(COOX)—CH$_2$(COOX); and X is H or a salt-forming cation. For example, if in the above general formula A and B are both H, then the compound is oxydissuccinic acid and its water-soluble salts. If A is OH and B is H, then the compound is tartrate monosuccinic acid (TMS) and its water-soluble salts. If A is H and B is —O—CH(COOX)—CH$_2$(COOX), then the compound is tartrate disuccinic acid (TDS) and its water-soluble salts. Mixtures of these builders are especially preferred for use herein. Particularly preferred are mixtures of TMS and TDS in a weight ratio of TMS to TDS of from about 97:3 to about 20:80. These builders are disclosed in U.S. Pat. No. 4,663,071, issued to Bush et al., on May 5, 1987.

Suitable ether polycarboxylates also include cyclic compounds, particularly alicyclic compounds, such as those described in U.S. Pat. Nos. 3,923,679; 3,835,163; 4,158,635; 4,120,874 and 4,102,903, all of which are incorporated herein by reference.

Other useful detergency builders include the ether hydroxypolycarboxylates represented by the structure:

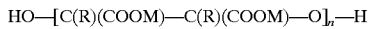

HO—[C(R)(COOM)—C(R)(COOM)—O]$_n$—H wherein M is hydrogen or a cation wherein the resultant salt is water-soluble, preferably an alkali metal, ammonium or substituted ammonium cation, n is from about 2 to about 15 (preferably n is from about 2 to about 10, more preferably n averages from about 2 to about 4) and each R is the same or different and selected from hydrogen, C$_{1-4}$ alkyl or C$_{1-4}$ substituted alkyl (preferably R is hydrogen).

Still other ether polycarboxylates include copolymers of maleic anhydride with ethylene or vinyl methyl ether, 1,3,5-trihydroxy benzene-2,4,6-trisulphonic acid, and carboxymethyloxysuccinic acid.

Organic polycarboxylate builders also include the various alkali metal, ammonium and substituted ammonium salts of polyacetic acids. Examples include the sodium, potassium, lithium, ammonium and substituted ammonium salts of ethylenediamine tetraacetic acid, and nitrilotriacetic acid.

Also included are polycarboxylates such as mellitic acid, succinic acid, oxydisuccinic acid, polymaleic acid, benzene 1,3,5-tricarboxylic acid, and carboxymethyloxysuccinic acid, and soluble salts thereof.

Citrate builders, e.g., citric acid and soluble salts thereof (particularly sodium salt), are polycarboxylate builders of particular importance for heavy duty liquid detergent formulations, but can also be used in granular compositions.

Other carboxylate builders include the carboxylated carbohydrates disclosed in U.S. Pat. No. 3,723,322, Diehl, issued Mar. 28, 1973, incorporated herein by reference.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986, incorporated herein by reference. Useful succinic acid builders include the $C_5$–$C_{20}$ alkyl succinic acids and salts thereof. A particularly preferred compound of this type is dodecenylsuccinic acid. Alkyl succinic acids typically are of the general formula

i.e., derivatives of succinic acid, wherein R is hydrocarbon, e.g., $C_{10}$–$C_{20}$ alkyl or alkenyl, preferably $C_{12}$–$C_{16}$ or wherein R may be substituted with hydroxyl, sulfo, sulfoxy or sulfone substituents, all as described in the above-mentioned patents.

The succinate builders are preferably used in the form of their water-soluble salts, including the sodium, potassium, ammonium and alkanolammonium salts.

Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Examples of useful builders also include sodium and potassium carboxymethyloxymalonate, carboxymethyloxysuccinate, cis-cyclo-hexane-hexacarboxylate, cis-cyclopentane-tetracarboxylate, water-soluble polyacrylates (these polyacrylates having molecular weights to above about 2,000 can also be effectively utilized as dispersants), and the copolymers of maleic anhydride with vinyl methyl ether or ethylene.

Other suitable polycarboxylates are the polyacetal carboxylates disclosed in U.S. Pat. No. 4,144,226, Crutchfield et al., issued Mar. 13, 1979, incorporated herein by reference. These polyacetal carboxylates can be prepared by bringing together, under polymerization conditions, an ester of glyoxylic acid and a polymerization initiator. The resulting polyacetal carboxylate ester is then attached to chemically stable end groups to stabilize the polyacetal carboxylate against rapid depolymerization in alkaline solution, converted to the corresponding salt, and added to a surfactant.

Polycarboxylate builders are also disclosed in U.S. Pat. No. 3,308,067, Diehl, issued Mar. 7, 1967, incorporated herein by reference. Such materials include the water-soluble salts of homo- and copolymers of aliphatic carboxylic acids such as maleic acid, itaconic acid and methylenemalonic acid.

Other organic builders known in the art can also be used. For example, monocarboxylic acids, and soluble salts thereof, having long chain hydrocarbyls can be utilized. These would include materials generally referred to as "soaps." Chain lengths of $C_{10}$–$C_{20}$ are typically utilized. The hydrocarbyls can be saturated or unsaturated.

Other optional ingredients include chelating agents, clay soil removal/anti redeposition agents, polymeric dispersing agents, bleaches, brighteners, suds suppressors, solvents and aesthetic agents.

VI Working Examples of Compositions

The detergent composition herein can be formulated as a variety of compositions, for instance as laundry detergents as well as hard surface cleaners or dishwashing compositions.

1. Hard Surface Cleaning Compositions

As used herein "hard surface cleaning composition" refers to liquid and granular detergent compositions for cleaning hard surfaces such as floors, walls, bathroom tile, and the like. Hard surface cleaning compositions of the present invention comprise an effective amount of one or more variants of the present invention, preferably from about 0.001% to about 10%, more preferably from about 0.01% to about 5%, more preferably still from about 0.05% to about 1% by weight of variant of the composition. In addition to comprising one or more of the variants, such hard surface cleaning compositions typically comprise a surfactant and a water-soluble sequestering builder. In certain specialized products such as spray window cleaners, however, the surfactants are sometimes not used since they may produce a filmy/streaky residue on the glass surface.

The surfactant component, when present, may comprise as little as 0.1% of the compositions herein, but typically the compositions will contain from about 0.25% to about 10%, more preferably from about 1% to about 5% of surfactant.

Typically the compositions will contain from about 0.5% to about 50% of a detergency builder, preferably from about 1% to about 10%.

Preferably the pH should be in the range of about 8 to 12. Conventional pH adjustment agents such as sodium hydroxide, sodium carbonate or hydrochloric acid can be used if adjustment is necessary.

Solvents may be included in the compositions. Useful solvents include, but are not limited to, glycol ethers such as diethyleneglycol monohexyl ether, diethyleneglycol monobutyl ether, ethyleneglycol monobutyl ether, ethyleneglycol monohexyl ether, propyleneglycol monobutyl ether, dipropyleneglycol monobutyl ether, and diols such as 2,2,4-trimethyl-1,3-pentanediol and 2-ethyl-1,3-hexanediol. When used, such solvents are typically present at levels of from about 0.5% to about 15%, preferably from about 3% to about 11%.

Additionally, highly volatile solvents such as isopropanol or ethanol can be used in the present compositions to facilitate faster evaporation of the composition from surfaces when the surface is not rinsed after "full strength" application of the composition to the surface. When used, volatile solvents are typically present at levels of from about 2% to about 12% in the compositions.

Suitable hard surface cleaning composition embodiments of the present invention are illustrated by the following examples.

Liquid Hard Surface Cleaning Compositions

| Component | Example No. 7 | 8 | 9 | 10 | 11 | 12 |
|---|---|---|---|---|---|---|
| Variant 1/Subtilisin | 0.05 | 0.50 | 0.02 | 0.03 | 0.10 | 0.03 |
| Variant 2/Subtilisin | — | — | — | — | 0.20 | 0.02 |
| $Na_2$DIDA* | | | | | | |
| EDTA** | — | — | 2.90 | 2.90 | — | — |
| Na Citrate | — | — | — | — | 2.90 | 2.90 |
| $NaC_{12}$ Alkyl-benzene sulfonate | 1.95 | — | 1.95 | — | 1.95 | — |
| $NaC_{12}$ Alkylsulfate | — | 2.20 | — | 2.20 | — | 2.20 |
| $NaC_{12}$(ethoxy)*** sulfate | — | 2.20 | — | 2.20 | — | 2.20 |
| $C_{12}$ Dimethylamine oxide | — | 0.50 | — | 0.50 | — | 0.50 |
| Na Cumene sulfonate | 1.30 | — | 1.30 | — | 1.30 | — |
| Hexyl Carbitol*** | 6.30 | 6.30 | 6.30 | 6.30 | 6.30 | 6.30 |
| Water**** | balance to 100% | | | | | |

*Disodium N-diethyleneglycol-N,N-iminodiacetate
**$Na_4$ ethylenediamine diacetic acid
***Diethyleneglycol monohexyl ether
****All formulas adjusted to pH 7

In the examples above any of the variants recited or claimed are substituted for the variant(s) shown above, with substantially similar results.

Spray Compositions for Cleaning Hard Surfaces and Removing Household Mildew

| Component | Example No. 13 | 14 | 15 | 16 | 17 | 18 |
|---|---|---|---|---|---|---|
| Variant 1/Subtilisin | 0.50 | 0.05 | 0.60 | 0.30 | 0.20 | 0.30 |
| Variant 2/Subtilisin | — | — | — | — | 0.30 | 0.10 |
| Sodium octyl sulfate | 2.00 | 2.00 | 2.00 | 2.00 | 2.00 | 2.00 |
| Sodium dodecyl sulfate | 4.00 | 4.00 | 4.00 | 4.00 | 4.00 | 4.00 |
| Sodium hydroxide | 0.80 | 0.80 | 0.80 | 0.80 | 0.80 | 0.80 |
| Silicate (Na) | 0.04 | 0.04 | 0.04 | 0.04 | 0.04 | 0.04 |
| Perfume | 0.35 | 0.35 | 0.35 | 0.35 | 0.35 | 0.35 |
| Water | balance to 100% | | | | | |

Product pH is adjusted to 7.

In the examples above any of the variants recited or claimed are substituted for the variant(s) shown above, with substantially similar results.

2. Dishwashing Compositions

In another embodiment of the present invention, dishwashing compositions comprise one or more variants of the present invention. As used herein, "dishwashing composition" refers to all forms for compositions for cleaning dishes, including but not limited to, granular, gel, and liquid forms. Suitable dishwashing composition embodiments of the present invention are illustrated by the following examples.

Dishwashing Composition

| Component | Example No. 19 | 20 | 21 | 22 | 23 | 24 |
|---|---|---|---|---|---|---|
| Variant 1/Subtilisin | 0.05 | 0.50 | 0.02 | 0.40 | 0.10 | 0.03 |
| Variant 2/Subtilisin | — | — | — | — | 0.40 | 0.02 |
| $C_{12}$–$C_{14}$ N-methyl-glucamide | 0.90 | 0.90 | 0.90 | 0.90 | 0.90 | 0.90 |
| $C_{12}$ ethoxy (1) sulfate | 12.00 | 12.00 | 12.00 | 12.00 | 12.00 | 12.00 |
| 2-methyl undecanoic acid | 4.50 | 4.50 | 4.50 | 4.50 | 4.50 | 4.50 |
| $C_{12}$ ethoxy (2) carboxylate | 4.50 | 4.50 | 4.50 | 4.50 | 4.50 | 4.50 |
| $C_{12}$ alcohol ethoxylate (4) | 3.00 | 3.00 | 3.00 | 3.00 | 3.00 | 3.00 |
| $C_{12}$ amine oxide | 3.00 | 3.00 | 3.00 | 3.00 | 3.00 | 3.00 |
| Sodium cumene sulfonate | 2.00 | 2.00 | 2.00 | 2.00 | 2.00 | 2.00 |
| Ethanol | 4.00 | 4.00 | 4.00 | 4.00 | 4.00 | 4.00 |
| $Mg^{++}$ (as $MgCl_2$) | 0.20 | 0.20 | 0.20 | 0.20 | 0.20 | 0.20 |
| $Ca^{++}$ (as $CaCl_2$) | 0.40 | 0.40 | 0.40 | 0.40 | 0.40 | 0.40 |
| Water | balance to 100% | | | | | |

Product pH is adjusted to 7.

In the examples above any of the variants recited or claimed are substituted for the variant(s) shown above, with substantially similar results.

3. Fabric Cleaning Compositions

In another embodiment of the present invention, fabric cleaning compositions comprise one or more variants of the present invention. As used herein, "fabric cleaning composition" refers to all forms for detergent compositions for cleaning fabrics, including but not limited to, granular, liquid and bar forms. Preferred fabric cleaning compositions are those in the liquid form.

a. Granular Fabric Cleaning Compositions

The granular fabric cleaning compositions of the present invention contain an effective amount of one or more variants of the present invention, preferably from about 0.001% to about 10%, more preferably from about 0.005% to about 5%, more preferably from about 0.01% to about 1% by weight of active of the composition. In addition to one or more variants, the granular fabric cleaning compositions typically comprise at least one surfactant, one or more builders, and, in some cases, a bleaching agent.

Suitable granular fabric cleaning composition embodiments of the present invention are illustrated by the following examples.

Examples 25–28

Granular Fabric Cleaning Composition

| Component | Example No. 25 | 26 | 27 | 28 |
|---|---|---|---|---|
| Variant 1/Subtilisin | 0.10 | 0.20 | 0.03 | 0.05 |
| Variant 4/Subtilisin | — | — | 0.02 | 0.05 |
| $C_{13}$ linear alkyl benzene sulfonate | 22.00 | 22.00 | 22.00 | 22.00 |
| Phosphate (as sodium tripolyphosphates) | 23.00 | 23.00 | 23.00 | 23.00 |
| Sodium carbonate | 23.00 | 23.00 | 23.00 | 23.00 |
| Sodium silicate | 14.00 | 14.00 | 14.00 | 14.00 |
| Zeolite | 8.20 | 8.20 | 8.20 | 8.20 |
| Chelant (diethylaenetriamine-pentaacetic acid) | 0.40 | 0.40 | 0.40 | 0.40 |
| Sodium sulfate | 5.50 | 5.50 | 5.50 | 5.50 |
| Water | balance to 100% | | | |

In the examples above any of the variants recited or claimed are substituted for the variant(s) shown above, with substantially similar results.

Examples 29–32

Granular Fabric Cleaning Composition

| Component | Example No. | | | |
|---|---|---|---|---|
| | 29 | 30 | 31 | 32 |
| Variant 2/Subtilisin | 0.10 | 0.20 | 0.03 | 0.05 |
| Variant 3/Subtilisin | — | — | 0.02 | 0.05 |
| $C_{12}$ alkyl benzene sulfonate | 12.00 | 12.00 | 12.00 | 12.00 |
| Zeolite A (1–10 micrometer) | 26.00 | 26.00 | 26.00 | 26.00 |
| 2-butyl octanoic acid | 4.00 | 4.00 | 4.00 | 4.00 |
| $C_{12}$–$C_{14}$ secondary (2,3) alkyl sulfate, Na salt | 5.00 | 5.00 | 5.00 | 5.00 |
| Sodium citrate | 5.00 | 5.00 | 5.00 | 5.00 |
| Optical brightener | 0.10 | 0.10 | 0.10 | 0.10 |
| Sodium sulfate | 17.00 | 17.00 | 17.00 | 17.00 |
| Water and minors | balance to 100% | | | |

In the examples above any of the variants recited or claimed are substituted for the variant(s) shown above, with substantially similar results.

Examples 33–36

Granular Fabric Cleaning Composition

| Component | Example No. | | | |
|---|---|---|---|---|
| | 33 | 34 | 35 | 36 |
| Variant 1/Subtilisin | 0.10 | 0.20 | 0.03 | 0.05 |
| Variant 2/Subtilisin | — | — | 0.02 | 0.05 |
| $C_{13}$ linear alkyl benzene sulfonate | 22.00 | 22.00 | 22.00 | 22.00 |
| Phosphate (as sodium tripolyphosphates) | 23.00 | 23.00 | 23.00 | 23.00 |
| Sodium carbonate | 23.00 | 23.00 | 23.00 | 23.00 |
| Sodium silicate | 14.00 | 14.00 | 14.00 | 14.00 |
| Zeolite | 8.20 | 8.20 | 8.20 | 8.20 |
| Chelant (diethylaenetriamine-pentaacetic acid) | 0.40 | 0.40 | 0.40 | 0.40 |
| Sodium sulfate | 5.50 | 5.50 | 5.50 | 5.50 |
| Water | balance to 100% | | | |

In the examples above any of the variants recited or claimed are substituted for the variant(s) shown above, with substantially similar results.

Examples 37–40

Granular Fabric Cleaning Composition

| Component | Example No. | | | |
|---|---|---|---|---|
| | 37 | 38 | 39 | 40 |
| Variant 1/Subtilisin | 0.10 | 0.20 | 0.03 | 0.05 |
| Variant 2/Subtilisin | — | — | 0.02 | 0.05 |
| $C_{12}$ alkyl benzene sulfonate | 12.00 | 12.00 | 12.00 | 12.00 |
| Zeolite A (1–10 micrometer) | 26.00 | 26.00 | 26.00 | 26.00 |
| 2-butyl octanoic acid | 4.00 | 4.00 | 4.00 | 4.00 |
| $C_{12}$–$C_{14}$ secondary (2,3) alkyl sulfate, Na salt | 5.00 | 5.00 | 5.00 | 5.00 |
| Sodium citrate | 5.00 | 5.00 | 5.00 | 5.00 |
| Optical brightener | 0.10 | 0.10 | 0.10 | 0.10 |
| Sodium sulfate | 17.00 | 17.00 | 17.00 | 17.00 |
| Water and minors | balance to 100% | | | |

In the examples above any of the variants recited or claimed are substituted for the variant(s) shown above, with substantially similar results.

Examples 41–42

Granular Fabric Cleaning Composition

| Component | Example No. | |
|---|---|---|
| | 41 | 42 |
| Linear alkyl benzene sulphonate | 11.4 | 10.70 |
| Tallow alkyl sulphate | 1.80 | 2.40 |
| $C_{14-15}$ alkyl sulphate | 3.00 | 3.10 |
| $C_{14-15}$ alcohol 7 times ethoxylated | 4.00 | 4.00 |
| Tallow alcohol 11 times ethoxylated | 1.80 | 1.80 |
| Dispersant | 0.07 | 0.1 |
| Silicone fluid | 0.80 | 0.80 |
| Trisodium citrate | 14.00 | 15.00 |
| Citric acid | 3.00 | 2.50 |
| Zeolite | 32.50 | 32.10 |
| Maleic acid acrylic acid copolymer | 5.00 | 5.00 |
| Diethylene triamine penta methylene phosphonic acid | 1.00 | 0.20 |
| Variant 1/Subtilisin | 0.30 | 0.30 |
| Lipase | 0.36 | 0.40 |
| Amylase | 0.30 | 0.30 |
| Sodium silicate | 2.00 | 2.50 |
| Sodium sulphate | 3.50 | 5.20 |
| Polyvinyl pyrrolidone | 0.30 | 0.50 |
| Perborate | 0.5 | 1 |
| Phenol sulphonate | 0.1 | 0.2 |
| Peroxidase | 0.1 | 0.1 |
| Minors | Up to 100 | Up to 100 |

In the examples above any of the variants recited or claimed are substituted for the variant(s) shown above, with substantially similar results.

Examples 43–44

Granular Fabric Cleaning Composition

| Component | Example No. | |
|---|---|---|
| | 43 | 44 |
| Sodium linear $C_{12}$ alkyl benzene-sulfonate | 6.5 | 8.0 |
| Sodium sulfate | 15.0 | 18.0 |
| Zeolite A | 26.0 | 22.0 |
| Sodium nitrilotriacetate | 5.0 | 5.0 |
| Polyvinyl pyrrolidone | 0.5 | 0.7 |
| Tetraacetylethylene diamine | 3.0 | 3.0 |
| Boric acid | 4.0 | — |
| Perborate | 0.5 | 1 |
| Phenol sulphonate | 0.1 | 0.2 |
| Variant 2/Subtilisin | 0.4 | 0.4 |
| Fillers (e.g., silicates; carbonates; perfumes; water) | Up to 100 | Up to 100 |

In the examples above any of the variants recited or claimed are substituted for the variant(s) shown above, with substantially similar results.

Example 45

Compact Granular Fabric Cleaning Composition

| Component | Weight % |
|---|---|
| Alkyl Sulphate | 8.0 |
| Alkyl Ethoxy Sulphate | 2.0 |

Compact Granular Fabric Cleaning Composition

| Component | Weight % |
|---|---|
| Mix of $C_{25}$ and $C_{45}$ alcohol 3 and 7 times ethoxylated | 6.0 |
| Polyhydroxy fatty acid amide | 2.5 |
| Zeolite | 17.0 |
| Layered silicate/citrate | 16.0 |
| Carbonate | 7.0 |
| Maleic acid acrylic acid copolymer | 5.0 |
| Soil release polymer | 0.4 |
| Carboxymethyl cellulose | 0.4 |
| Poly (4-vinylpyridine)-N-oxide | 0.1 |
| Copolymer of vinylimidazole and vinylpyrrolidone | 0.1 |
| PEG2000 | 0.2 |
| Pro209Gln | 0.5 |
| Lipase | 0.2 |
| Cellulase | 0.2 |
| Tetracetylethylene diamine | 6.0 |
| Percarbonate | 22.0 |
| Ethylene diamine disuccinic acid | 0.3 |
| Suds suppressor | 3.5 |
| Disodium-4,4'-bis (2-morpholino-4-anilino-s-triazin-6-ylamino) stilbene-2,2'-disulphonate | 0.25 |
| Disodium-4,4'-bis (2-sulfostyril) biphenyl | 0.05 |
| Water, Perfume and Minors | Up to 100 |

In the example above any of the variants recited or claimed are substituted for the variant(s) shown above, with substantially similar results.

Example 46

Granular Fabric Cleaning Composition

| Component | Weight % |
|---|---|
| Linear alkyl benzene sulphonate | 7.6 |
| $C_{16}$–$C_{18}$ alkyl sulfate | 1.3 |
| $C_{14–15}$ alcohol 7 times ethoxylated | 4.0 |
| Coco-alkyl-dimethyl hydroxyethyl ammonium chloride | 1.4 |
| Dispersant | 0.07 |
| Silicone fluid | 0.8 |
| Trisodium citrate | 5.0 |
| Zeolite 4A | 15.0 |
| Maleic acid acrylic acid copolymer | 4.0 |
| Diethylene triamine penta methylene phosphonic acid | 0.4 |
| Perborate | 15.0 |
| Tetraacetylethylene diamine | 5.0 |
| Smectite clay | 10.0 |
| Poly (oxy ethylene) (MW 300,000) | 0.3 |
| Variant 1/Subtilisin | 0.4 |
| Lipase | 0.2 |
| Amylase | 0.3 |
| Cellulase | 0.2 |
| Sodium silicate | 3.0 |
| Sodium carbonate | 10.0 |
| Carboxymethyl cellulose | 0.2 |
| Brighteners | 0.2 |
| Water, perfume and minors | Up to 100 |

In the example above any of the variants recited or claimed are substituted for the variant(s) shown above, with substantially similar results.

Example 47

Granular Fabric Cleaning Composition

| Component | Weight % |
|---|---|
| Linear alkyl benzene sulfonate | 6.92 |
| Tallow alkyl sulfate | 2.05 |
| $C_{14–15}$ alcohol 7 times ethoxylated | 4.4 |
| $C_{12–15}$ alkyl ethoxy sulfate-3 times ethoxylated | 0.16 |
| Zeolite | 20.2 |
| Citrate | 5.5 |
| Carbonate | 15.4 |
| Silicate | 3.0 |
| Maleic acid acrylic acid copolymer | 4.0 |
| Carboxymethyl cellulase | 0.31 |
| Soil release polymer | 0.30 |
| Variant 1/Subtilisin | 0.2 |
| Lipase | 0.36 |
| Cellulase | 0.13 |
| Perborate tetrahydrate | 11.64 |
| Perborate monohydrate | 8.7 |
| Tetraacetylethylene diamine | 5.0 |
| Diethylene triamine penta methyl phosphonic acid | 0.38 |
| Magnesium sulfate | 0.40 |
| Brightener | 0.19 |
| Perfume, silicone, suds suppressors | 0.85 |
| Minors | Up to 100 |

In the examples above any of the variants recited or claimed are substituted for the variant(s) shown above, with substantially similar results.

b. Liquid Fabric Cleaning Compositions

Liquid fabric cleaning compositions of the present invention comprise an effective amount of one or more variants of the present invention, preferably from about 0.005% to about 5%, more preferably from about 0.01% to about 1%, by weight of active of the composition. Such liquid fabric cleaning compositions typically additionally comprise an anionic surfactant, a fatty acid, a water-soluble detergency builder and water.

Suitable liquid fabric cleaning composition embodiments of the present invention are illustrated by the following examples.

Examples 48–52

Liquid Fabric Cleaning Compositions

| | Example No. | | | | |
|---|---|---|---|---|---|
| Component | 48 | 49 | 50 | 51 | 52 |
| Variant 1/Subtilisin | 0.05 | 0.03 | 0.30 | 0.03 | 0.10 |
| Variant 2/Subtilisin | — | — | — | 0.01 | 0.20 |
| $C_{12}$–$C_{14}$ alkyl sulfate, Na | 20.00 | 20.00 | 20.00 | 20.00 | 20.00 |
| 2-butyl octanoic acid | 5.00 | 5.00 | 5.00 | 5.00 | 5.00 |
| Sodium citrate | 1.00 | 1.00 | 1.00 | 1.00 | 1.00 |
| $C_{10}$ alcohol ethoxylate (3) | 13.00 | 13.00 | 13.00 | 13.00 | 13.00 |
| Monethanolamine | 2.50 | 2.50 | 2.50 | 2.50 | 2.50 |
| Water/propylene glycol/ethanol (100:1:1) | balance to 100% | | | | |

In the examples above any of the variants recited or claimed are substituted for the variant(s) shown above, with substantially similar results.

Examples 53–57

Liquid Fabric Cleaning Compositions

| Component | \multicolumn{5}{c}{Example No.} | | | | |
|---|---|---|---|---|---|
| | 53 | 54 | 55 | 56 | 57 |
| Variant 3/Subtilisin | 0.05 | 0.03 | 0.30 | 0.03 | 0.10 |
| Variant 7/Subtilisin | — | — | — | 0.01 | 0.20 |
| $C_{12}$–$C_{14}$ alkyl sulfate, Na | 20.00 | 20.00 | 20.00 | 20.00 | 20.00 |
| 2-butyl octanoic acid | 5.00 | 5.00 | 5.00 | 5.00 | 5.00 |
| Sodium citrate | 1.00 | 1.00 | 1.00 | 1.00 | 1.00 |
| $C_{10}$ alcohol ethoxylate (3) | 13.00 | 13.00 | 13.00 | 13.00 | 13.00 |
| Monethanolamine | 2.50 | 2.50 | 2.50 | 2.50 | 2.50 |
| Water/propylene glycol/ethanol (100:1:1) | \multicolumn{5}{c}{balance to 100%} | | | | |

In the examples above any of the variants recited or claimed are substituted for the variant(s) shown above, with substantially similar results.

Examples 58–59

Granular Fabric Cleaning Composition

| Component | Example No. | |
|---|---|---|
| | 58 | 59 |
| $C_{12-14}$ alkenyl succinic acid | 3.0 | 8.0 |
| Citric acid monohydrate | 10.0 | 15.0 |
| Sodium $C_{12-15}$ alkyl sulphate | 8.0 | 8.0 |
| Sodium sulfate of $C_{12-15}$ alcohol 2 times ethoxylated | — | 3.0 |
| $C_{12-15}$ alcohol 7 times ethoxylated | — | 8.0 |
| $C_{12-15}$ alcohol 5 times ethoxylated | 8.0 | — |
| Diethylene triamine penta (methylene phosphonic acid) | 0.2 | — |
| Oleic acid | 1.8 | — |
| Ethanol | 4.0 | 4.0 |
| Propanediol | 2.0 | 2.0 |
| Variant 11/Subtilisin | 0.2 | 0.2 |
| Polyvinyl pyrrolidone | 1.0 | 2.0 |
| Suds suppressor | 0.15 | 0.15 |
| NaOH | \multicolumn{2}{c}{up to pH 7.5} | |
| Perborate | 0.5 | 1 |
| Phenol sulphonate | 0.1 | 0.2 |
| Peroxidase | 0.4 | 0.1 |
| Waters and minors | \multicolumn{2}{c}{up to 100 parts} | |

In the examples above any of the variants recited or claimed are substituted for the variant(s) shown above, with substantially similar results.

Examples 60–62

Liquid Fabric Cleaning Composition

| Component | Example No. | | |
|---|---|---|---|
| | 60 | 61 | 62 |
| Citric Acid | 7.10 | 3.00 | 3.00 |
| Fatty Acid | 2.00 | — | 2.00 |
| Ethanol | 1.93 | 3.20 | 3.20 |
| Boric Acid | 2.22 | 3.50 | 3.50 |
| Monoethanolamine | 0.71 | 1.09 | 1.09 |
| 1,2 Propanediol | 7.89 | 8.00 | 8.00 |
| NaCumene Sulfonate | 1.80 | 3.00 | 3.00 |
| NaFormate | 0.08 | 0.08 | 0.08 |
| NaOH | 6.70 | 3.80 | 3.80 |
| Silicon anti-foam agent | 1.16 | 1.18 | 1.18 |
| Variant 6/Subtilisin | 0.0145 | — | — |
| Variant 4/Subtilisin | — | 0.0145 | — |
| Variant 3/Subtilisin | — | — | 0.0145 |
| Lipase | 0.200 | 0.200 | 0.200 |
| Cellulase | — | 7.50 | 7.50 |
| Soil release polymer | 0.29 | 0.15 | 0.15 |
| Anti-foaming agents | 0.06 | 0.085 | 0.085 |
| Brightener 36 | 0.095 | — | — |
| Brightener 3 | — | 0.05 | 0.05 |
| $C_{12}$ alkyl benzenesulfonic acid | 9.86 | — | — |
| $C_{12-15}$ alkyl polyethoxylate (2.5) sulfate | 13.80 | 18.00 | 18.00 |
| $C_{12}$ glucose amide | — | 5.00 | 5.00 |
| $C_{12-13}$ alkyl polyethoxylate (9) | 2.00 | 2.00 | 2.00 |
| Water, perfume and minors | \multicolumn{3}{c}{balance to 100%} | | |

In the examples above any of the variants recited or claimed are substituted for the variant(s) shown above, with substantially similar results.

c. Bar Fabric Cleaning Compositions

Bar fabric cleaning compositions of the present invention suitable for hand-washing soiled fabrics contain an effective amount of one or more variants of the present invention, preferably from about 0.001% to about 10%, more preferably from about 0.01% to about 1% by weight of the composition.

Suitable bar fabric cleaning composition embodiments of the present invention are illustrated by the following examples.

Examples 63–66

Bar Fabric Cleaning Compositions

| Component | Example No. | | | |
|---|---|---|---|---|
| | 63 | 64 | 65 | 66 |
| Variant 1/Subtilisin | 0.3 | — | 0.1 | 0.02 |
| Variant 2/Subtilisin | — | — | 0.4 | 0.03 |
| $C_{12}$–$C_{16}$ alkyl sulfate, Na | 20.0 | 20.0 | 20.0 | 20.00 |
| $C_{12}$–$C_{14}$ N-methyl glucamide | 5.0 | 5.0 | 5.0 | 5.00 |
| $C_{11}$–$C_{13}$ alkyl benzene sulfonate, Na | 10.0 | 10.0 | 10.0 | 10.00 |
| Sodium carbonate | 25.0 | 25.0 | 25.0 | 25.00 |
| Sodium pyrophosphate | 7.0 | 7.0 | 7.0 | 7.00 |
| Sodium tripolyphosphate | 7.0 | 7.0 | 7.0 | 7.00 |
| Zeolite A (0.1–.10) | 5.0 | 5.0 | 5.0 | 5.00 |
| Carboxymethylcellulose | 0.2 | 0.2 | 0.2 | 0.20 |
| Polyacrylate (MW 1400) | 0.2 | 0.2 | 0.2 | 0.20 |
| Coconut monethanolamide | 5.0 | 5.0 | 5.0 | 5.00 |
| Brightener, perfume | 0.2 | 0.2 | 0.2 | 0.20 |
| $CaSO_4$ | 1.0 | 1.0 | 1.0 | 1.00 |
| $MgSO_4$ | 1.0 | 1.0 | 1.0 | 1.00 |
| Water | 4.0 | 4.0 | 4.0 | 4.00 |
| Filler* | \multicolumn{4}{c}{balance to 100%} | | | |

*Can be selected from convenient materials such as $CaCO_3$, talc, clay, silicates, and the like.

In the examples above any of the variants recited or claimed are substituted for the variant(s) shown above, with substantially similar results.

Examples 67–70

| Bar Fabric Cleaning Compositions | | | | |
|---|---|---|---|---|
| | Example No. | | | |
| Component | 67 | 68 | 69 | 70 |
| Variant 1/Subtilisin | 0.3 | — | 0.1 | 0.02 |
| Variant 9/Subtilisin | — | 0.3 | 0.4 | 0.03 |
| $C_{12}$–$C_{16}$ alkyl sulfate, Na | 20.0 | 20.0 | 20.0 | 20.00 |
| $C_{12}$–$C_{14}$ N-methyl glucamide | 5.0 | 5.0 | 5.0 | 5.00 |
| $C_{11}$–$C_{13}$ alkyl benzene sulfonate, Na | 10.0 | 10.0 | 10.0 | 10.00 |
| Sodium carbonate | 25.0 | 25.0 | 25.0 | 25.00 |
| Sodium pyrophosphate | 7.0 | 7.0 | 7.0 | 7.00 |
| Sodium tripolyphosphate | 7.0 | 7.0 | 7.0 | 7.00 |
| Zeolite A (0.1–.10) | 5.0 | 5.0 | 5.0 | 5.00 |
| Carboxymethylcellulose | 0.2 | 0.2 | 0.2 | 0.20 |
| Polyacrylate (MW 1400) | 0.2 | 0.2 | 0.2 | 0.20 |
| Coconut monethanolamide | 5.0 | 5.0 | 5.0 | 5.00 |
| Brightener, perfume | 0.2 | 0.2 | 0.2 | 0.20 |
| $CaSO_4$ | 1.0 | 1.0 | 1.0 | 1.00 |
| $MgSO_4$ | 1.0 | 1.0 | 1.0 | 1.00 |
| Water | 4.0 | 4.0 | 4.0 | 4.00 |
| Filler* | balance to 100% | | | |

*Can be selected from convenient materials such as $CaCO_3$, talc, clay, silicates, and the like.

In the examples above any of the variants recited or claimed are substituted for the variant(s) shown above, with substantially similar results.

B. Additional Cleaning Compositions

In addition to the hard surface cleaning, dishwashing and fabric cleaning compositions discussed above, one or more variants of the present invention may be incorporated into a variety of other cleaning compositions where hydrolysis of an insoluble substrate is desired. Such additional cleaning compositions include but are not limited to, oral cleaning compositions, denture cleaning compositions, and contact lens cleaning compositions.

1. Oral Cleaning Compositions

In another embodiment of the present invention, a pharmaceutically-acceptable amount of one or more variants of the present invention are included in compositions useful for removing peptide stains from teeth or dentures. As used herein, "oral cleaning compositions" refers to dentifrices, toothpastes, toothgels, toothpowders, mouthwashes, mouth sprays, mouth gels, chewing gums, lozenges, sachets, tablets, biogels, prophylaxis pastes, dental treatment solutions, and the like. Preferably, the oral cleaning compositions comprise from about 0.0001% to about 20% of one or more variants of the present invention, more preferably from about 0.001% to about 10%, more preferably still from about 0.01% to about 5%, by weight of the composition, and a pharmaceutically-acceptable carrier. As used herein, "pharmaceutically-acceptable" means that drugs, medicaments or inert ingredients which the term describes are suitable for use in contact with the tissues of humans and lower animals without undue toxicity, incompatibility, instability, irritation, allergic response, and the like, commensurate with a reasonable benefit/risk ratio.

Typically, the pharmaceutically-acceptable oral cleaning carrier components of the oral cleaning components of the oral cleaning compositions will generally comprise from about 50% to about 99.99%, preferably from about 65% to about 99.99%, more preferably from about 65% to about 99%, by weight of the composition.

The pharmaceutically-acceptable carrier components and optional components which may be included in the oral cleaning compositions of the present invention are well known to those skilled in the art. A wide variety of composition types, carrier components and optional components useful in the oral cleaning compositions are disclosed in U.S. Pat. No. 5,096,700, Seibel, issued Mar. 17, 1992; U.S. Pat. No. 5,028,414, Sampathkumar, issued Jul. 2, 1991; and U.S. Pat. No. 5,028,415, Benedict, Bush and Sunberg, issued Jul. 2, 1991; all of which are incorporated herein by reference.

Suitable oral cleaning composition embodiments of the present invention are illustrated by the following examples.

Examples 71–74

| Dentifrice Composition | | | | |
|---|---|---|---|---|
| | Example No. | | | |
| Component | 71 | 72 | 73 | 74 |
| Variant 1/Subtilisin | 2.000 | 3.500 | 1.500 | 2.000 |
| Sorbitol (70% aqueous solution) | 35.000 | 35.000 | 35.000 | 35.000 |
| PEG-6* | 1.000 | 1.000 | 1.000 | 1.000 |
| Silica dental abrasive** | 20.000 | 20.000 | 20.000 | 20.000 |
| Sodium fluoride | 0.243 | 0.243 | 0.243 | 0.243 |
| Titanium dioxide | 0.500 | 0.500 | 0.500 | 0.500 |
| Sodium saccharin | 0.286 | 0.286 | 0.286 | 0.286 |
| Sodium alkyl sulfate (27.9% aqueous solution) | 4.000 | 4.000 | 4.000 | 4.000 |
| Flavor | 1.040 | 1.040 | 1.040 | 1.040 |
| Carboxyvinyl Polymer*** | 0.300 | 0.300 | 0.300 | 0.300 |
| Carrageenan**** | 0.800 | 0.800 | 0.800 | 0.800 |
| Water | balance to 100% | | | |

*PE6-6 = Polyethylene glycol having a molecular weight of 600.
**Precipitated silica identified as Zeodent 119 offered by J.M. Huber.
***Carbopol offered by B.F. Goodrich Chemical Company.
****Iota Carrageenan offered by Hercules Chemical Company.

In the examples above any of the variants recited or claimed are substituted for the variant(s) shown above, with substantially similar results.

Examples 75–78

| Mouthwash Composition | | | | |
|---|---|---|---|---|
| | Example No. | | | |
| Component | 75 | 76 | 77 | 78 |
| Variant 10/Subtilisin | 3.00 | 7.50 | 1.00 | 5.00 |
| SDA 40 Alcohol | 8.00 | 8.00 | 8.00 | 8.00 |
| Flavor | 0.08 | 0.08 | 0.08 | 0.08 |
| Emulsifier | 0.08 | 0.08 | 0.08 | 0.08 |
| Sodium Fluoride | 0.05 | 0.05 | 0.05 | 0.05 |
| Glycerin | 10.00 | 10.00 | 10.00 | 10.00 |
| Sweetener | 0.02 | 0.02 | 0.02 | 0.02 |
| Benzoic acid | 0.05 | 0.05 | 0.05 | 0.05 |
| Sodium hydroxide | 0.20 | 0.20 | 0.20 | 0.20 |
| Dye | 0.04 | 0.04 | 0.04 | 0.04 |
| Water | balance to 100% | | | |

In the examples above any of the variants recited or claimed are substituted for the variant(s) shown above, with substantially similar results.

Examples 79–82

Lozenge Composition

| Component | Example No. 79 | 80 | 81 | 82 |
|---|---|---|---|---|
| Variant 8/Subtilisin | 0.01 | 0.03 | 0.10 | 0.02 |
| Sorbitol | 17.50 | 17.50 | 17.50 | 17.50 |
| Mannitol | 17.50 | 17.50 | 17.50 | 17.50 |
| Starch | 13.60 | 13.60 | 13.60 | 13.60 |
| Sweetener | 1.20 | 1.20 | 1.20 | 1.20 |
| Flavor | 11.70 | 11.70 | 11.70 | 11.70 |
| Color | 0.10 | 0.10 | 0.10 | 0.10 |
| Corn Syrup | | balance to 100% | | |

In the examples above any of the variants recited or claimed are substituted for the variant(s) shown above, with substantially similar results.

Examples 83–86

Chewing Gum Composition

| Component | Example No. 83 | 84 | 85 | 86 |
|---|---|---|---|---|
| Variant 1/Subtilisin | 0.03 | 0.02 | 0.10 | 0.05 |
| Sorbitol crystals | 38.44 | 38.40 | 38.40 | 38.40 |
| Paloja-T gum base* | 20.00 | 20.00 | 20.00 | 20.00 |
| Sorbitol (70% aqueous solution) | 22.00 | 22.00 | 22.00 | 22.00 |
| Mannitol | 10.00 | 10.00 | 10.00 | 10.00 |
| Glycerine | 7.56 | 7.56 | 7.56 | 7.56 |
| Flavor | 1.00 | 1.00 | 1.00 | 1.00 |

*Supplied by L.A. Dreyfus Company.

In the examples above any of the variants recited or claimed are substituted for the variant(s) shown above, with substantially similar results.

2. Denture Cleaning Compositions

In another embodiment of the present invention, denture cleaning compositions for cleaning dentures outside of the oral cavity comprise one or more variants of the present invention. Such denture cleaning compositions comprise an effective amount of one or more of the variants, preferably from about 0.0001% to about 50% of one or more of the variants, more preferably from about 0.001% to about 35%, more preferably still from about 0.01% to about 20%, by weight of the composition, and a denture cleansing carrier. Various denture cleansing composition formats such as effervescent tablets and the like are well known in the art (see for example U.S. Pat. No. 5,055,305, Young, incorporated herein by reference), and are generally appropriate for incorporation of one or more of the variants for removing peptide stains from dentures.

The denture cleaning composition embodiment of the present invention is illustrated by the following examples.

Examples 87–90

Two-layer Effervescent Denture Cleansing Tablet

| Component | Example No. 87 | 88 | 89 | 90 |
|---|---|---|---|---|
| Acidic Layer | | | | |
| Variant 4 | 1.0 | 1.5 | 0.01 | 0.05 |
| Tartaric acid | 24.0 | 24.0 | 24.00 | 24.00 |
| Sodium carbonate | 4.0 | 4.0 | 4.00 | 4.00 |
| Sulphamic acid | 10.0 | 10.0 | 10.00 | 10.00 |
| PEG 20,000 | 4.0 | 4.0 | 4.00 | 4.00 |
| Sodium bicarbonate | 24.5 | 24.5 | 24.50 | 24.50 |
| Potassium persulfate | 15.0 | 15.0 | 15.00 | 15.00 |
| Sodium acid pyrophosphate | 7.0 | 7.0 | 7.00 | 7.00 |
| Pyrogenic silica | 2.0 | 2.0 | 2.00 | 2.00 |
| TAED* | 7.0 | 7.0 | 7.00 | 7.00 |
| Ricinoleylsulfosuccinate | 0.5 | 0.5 | 0.50 | 0.50 |
| Flavor | 1.0 | 1.0 | 1.00 | 1.00 |
| Alkaline Layer | | | | |
| Sodium perborate monohydrate | 32.0 | 32.0 | 32.00 | 32.00 |
| Sodium bicarbonate | 19.0 | 19.0 | 19.00 | 19.00 |
| EDTA | 3.0 | 3.0 | 3.00 | 3.00 |
| Sodium tripolyphosphate | 12.0 | 12.0 | 12.00 | 12.00 |
| PEG 20,000 | 2.0 | 2.0 | 2.00 | 2.00 |
| Potassium persulfate | 26.0 | 26.0 | 26.00 | 26.00 |
| Sodium carbonate | 2.0 | 2.0 | 2.00 | 2.00 |
| Pyrogenic silica | 2.0 | 2.0 | 2.00 | 2.00 |
| Dye/flavor | 2.0 | 2.0 | 2.00 | 2.00 |

*Tetraacetylethylene diamine

In the examples above any of the variants recited or claimed are substituted for the variant(s) shown above, with substantially similar results.

3. Contact Lens Cleaning Compositions

In another embodiment of the present invention, contact lens cleaning compositions comprise one or more variants of the present invention. Such contact lens cleaning compositions comprise an effective amount of one or more of the variants, preferably from about 0.01% to about 50% of one or more of the variants, more preferably from about 0.01% to about 20%, more preferably still from about 1% to about 5%, by weight of the composition, and a contact lens cleaning carrier. Various contact lens cleaning composition formats such as tablets, liquids and the like are well known in the art (see for example U.S. Pat. No. 4,863,627, Davies, Meaken and Rees, issued Sep. 5, 1989; U.S. Pat. No. Re. 32,672, Huth, Lam and Kirai, reissued May 24, 1988; U.S. Pat. No. 4,609,493, Schäfer, issued Sep. 2, 1986; U.S. Pat. No. , 4,690,793, Ogunbiyi and Smith, issued Sep. 1, 1987; U.S. Pat. No. 4,614,549, Ogunbiyi, Riedhammer and Smith, issued Sep. 30, 1986; and U.S. Pat. No. 4,285,738, Ogata, issued Aug. 25, 1981; each of which are incorporated herein by reference), and are generally appropriate for incorporation of one or more variants of the present invention for removing peptide stains from contact lens.

Suitable contact lens cleaning composition embodiments of the present invention are illustrated by the following examples.

Examples 91–94

Enzymatic Contact Lens Cleaning Solution

| Component | 91 | 92 | 93 | 94 |
|---|---|---|---|---|
| Variant 11/Subtilisin | 0.01 | 0.5 | 0.1 | 2.0 |
| Glucose | 50.00 | 50.0 | 50.0 | 50.0 |
| Nonionic surfactant (polyoxyethlene-polyoxypropylene copolymer) | 2.00 | 2.0 | 2.0 | 2.0 |
| Anionic surfactant (polyoxyethylene-alkylphenylether sodium sulfricester) | 1.00 | 1.0 | 1.0 | 1.0 |
| Sodium chloride | 1.00 | 1.0 | 1.0 | 1.0 |
| Borax | 0.30 | 0.3 | 0.3 | 0.3 |
| Water | balance to 100% | | | |

In the examples above any of the variants recited or claimed are substituted for the variant(s) shown above, with substantially similar results.

Example 95

An inhibitor having a Ki value of $1 \times 10^8$, is used in a liquid cleaning composition according to example 47. Characterization of the composition shows that the composition has more than 85% of the protease activity after 1 month.

Upon use in a standard washing machine using a normal load and warm water it displays improved stain removal compared to the similar composition which differs only in using the wild type inhibitor rather than the variant. Similar results are seen in compositions according to examples 25–66.

All references cited in this application are hereby incorporated into it by reference.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

As is recognized in the art, there are occasionally errors in DNA and amino acid sequencing methods. As a result, the sequences encoded in the deposited material are incorporated herein by reference and controlling in the event of an error in any of the sequences found in the written description of the present invention. It is further noted that one of ordinary skill in the art reproducing Applicants' work from the written disclosure can discover any sequencing errors using routine skill. The deposit of ATCC No. 69955, 69956 and 69957 is not to be considered as an admission that the deposited material is essential to the practice of the present invention.

What is claimed is:

1. An isolated detergent stable peptide protease inhibitor variant of subtilisn inhibitor from Streptomyces of SEQ ID NO: 20 comprising a substitution mutation at position 83; wherein the substitution mutation provides a stabilized subtilisin inhibitor variant relative to the wild-type in a detergent composition.

2. A protease inhibitor variant according to claim 1 wherein said protease inhibitor variant further comprises a substitution at one or more position wherein at least one substitution occurs at positions 73, 47 and combination thereof of SEQ ID NO: 20.

3. A protease inhibitor variant according to claim 2 wherein the modified amino acid sequence has more than one substitution and provides for covalent dimerization of the inhibitor via disulfide bond formation.

4. A protease inhibitor variant according to claim 3 wherein the modification provides a variant suitable to inhibit the protease in the composition and still allows the inhibitor variant to dissociate from the protease upon dilution.

5. A protease inhibitor variant according to claim 3 wherein a modification is a residue from SEQ ID NO:20 and is chosen from the group consisting of M73D D83C-Variant 2
M73P D83C-Variant 3
M70Q D83C-Variant 5
M73P D83C S98A-Variant 6
M73P Y75A D83C-Variant 7
M73P D83C S98V-Variant 8
M70Q M73P D83C-Variant 9
M73P V74A D83C-Variant 10
M73P V74F D83C-Variant 11
M70Q D83C S98A-Variant 12
G47D M70Q D83C-Variant 13
G47D D83C S98A-Variant 14
G47D M73P D83C-Variant 15
G47D M73D D83C-Variant 16
M70Q M73P V74F D83C-Variant 17
M70Q M73P V74W D83C-Variant 18
M70Q M73P D83C S98A-Variant 19
G47D M73P V74F D83-Variant 20
G47D M73P V74W D83C-Variant 21
G47D M73P D83C S98A-Variant 22
G47D M70Q M73P V74F D83C-Variant 23
G47D M70Q M73P V74W D83C-Variant 24
G47D M73P V74F D83C S98A-Variant 25
G47D M73P V74W D83C S98A-Variant 26.

6. A cleaning composition comprising a protease and an inhibitor of claim 5.

7. A cleaning composition comprising the protease inhibitor variant of claim 1, protease and optionally a cleaning composition carrier.

8. The cleaning composition of claim 7, wherein the cleaning composition is a hard surface cleaning composition.

9. The cleaning composition of claim 7, wherein the cleaning composition is a fabric cleaning composition.

10. The fabric cleaning composition of claim 9, wherein the composition is in the form of a liquid.

11. The fabric cleaning composition of claim 10, wherein the composition comprises at least about 5% surfactant and at least about 5% builder, by weight of the composition, and further comprises one or more optional detergent ingredients.

12. DNA encoding the protease inhibitor variant of claim 1.

13. A vector comprising the DNA of claim 12.

14. An expression system comprising the DNA of claim 12, wherein said expression system includes plants and microorganisms only.

15. The expression system of claim 31 wherein the system is bacterial.

16. A liquid cleaning composition comprising from 1% to 80% of a surfactant, from 0.0001% to 1.0% of an active protease or a mixture of proteases, from 0.00001% to 5% of a protease inhibitor variant according to claim 1.

17. The cleaning composition of claim 23, wherein the protease to inhibitor ratio is from about 1:3 to about 1:1.

18. The cleaning composition of claim 17, wherein the protease to inhibitor ratio is from about 1:3 to about 1:1.5.

19. The cleaning composition of claim 18, wherein the protease to inhibitor ratio is about 1:2.

20. A test kit comprising the inhibitor of claim 1.

21. A method of making the inhibitor of claim 1 comprising the steps of:

a) growing an inhibitor expressing organism; and
b) purifying said inhibitor by one or more steps;
wherein said expressing organism includes plants and microorganisms only.

22. The method of making the inhibitor of claim 21 where the organism is a microorganism.

23. A protease inhibitor according to claim 1 in dry or concentrated liquid form.

24. A protease inhibitor according to claim 1 in dry or concentrated liquid form in a cleaning composition.

* * * * *

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
      (A) LENGTH: 360 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

```
GAATTCGATG CTCCTTCTGC ACTTTATGCA CCTTCAGCAT TAGTTTTAAC AGTTGGTAAA      60

GGAGTTAGCG CTACGACAGC TGCACCTGAA AGAGCAGTAA CTCTTACATG TGCTCCAGGC     120

CCTTCTGGTA CACATCCAGC AGCTGGCTCT GCATGTGCAG ATTTAGCTGC AGTAGGAGGT     180

GACTTAAACG CATTAACACG TGGTGAAGAC GTTATGTGTC CAATGGTTTA TGATCCTGTA     240

TTACTGACTG TTGATGGAGT TTGGCAAGGT AAACGCGTAT CTTATGAACG TGTATTTTCA     300

AATGAATGTG AAATGAACGC TCATGGCTCT TCTGTATTTG CATTTTAAGG ATCCAAGCTT     360
```

(2) INFORMATION FOR SEQ ID NO: 2:

(i) SEQUENCE CHARACTERISTICS:
      (A) LENGTH: 117 amino acids
      (B) TYPE: amino acid
      (C) STRANDEDNESS: not relevant
      (D) TOPOLOGY: linear (ii) MOLECULE TYPE: protein (xi) SEQUENCE DESCRIPTION: SEQ ID NO: 2:

Ala Gly Glu Phe Asp Ala Pro Ser Ala Leu Tyr Ala Pro Ser Ala Le
1               5                   10                  15

Val Leu Thr Val Gly Lys Gly Val Ser Ala Thr Thr Ala Ala Pro Gl
            20                  25                  30

Arg Ala Val Thr Leu Thr Cys Ala Pro Gly Pro Ser Gly Thr His Pr
        35                  40                  45

Ala Ala Gly Ser Ala Cys Ala Asp Leu Ala Ala Val Gly Gly Asp Le
    50                  55                  60

Asn Ala Leu Thr Arg Gly Glu Asp Val Met Cys Pro Met Val Tyr As
65                  70                  75                  80

Pro Val Leu Leu Thr Val Asp Gly Val Trp Gln Gly Lys Arg Val Se
                85                  90                  95

Tyr Glu Arg Val Phe Ser Asn Glu Cys Glu Met Asn Ala His Gly Se
            100                 105                 110

Ser Val Phe Ala Phe
        115

(2) INFORMATION FOR SEQ ID NO: 3:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

TCCGACGAAT TCGATGCTCC TTCTGCACTT TATGCACCTT CAGCATTAGT TTTAACAGTT       60

(2) INFORMATION FOR SEQ ID NO: 4:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

CCTGAAAGAG CAGTAACTCT TACATGTGCT CCAGGCCCTT CTGGTACACA TCCAGCAGCT       60

(2) INFORMATION FOR SEQ ID NO: 5:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

ACCTCCTACT GCAGCTAAAT CTGCACATGC AGAGCCAGCT GCTGGATGTG T       51

(2) INFORMATION FOR SEQ ID NO: 6:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

TACTGCTCTT TCAGGTGCAG CTGTCGTAGC GCTAACTCCT TTACCAACTG TTAAAACTA      A60

(2) INFORMATION FOR SEQ ID NO: 7:

(i) SEQUENCE CHARACTERISTICS:
      (A) LENGTH: 60 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 7:

GATTTAGCTG CAGTAGGAGG TGACTTAAAC GCATTAACAC GTGGTGAAGA CGTTATGTG      T60

(2) INFORMATION FOR SEQ ID NO: 8:

(i) SEQUENCE CHARACTERISTICS:
      (A) LENGTH: 60 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 8:

GTTGATGGAG TTTGGCAAGG TAAACGCGTA TCTTATGAAC GTGTATTTTC AAATGAATG      T60

(2) INFORMATION FOR SEQ ID NO: 9:

(i) SEQUENCE CHARACTERISTICS:
      (A) LENGTH: 72 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 9:

TGTCCAAAGC TTGGATCCTT AAAATGCAAA TACAGAAGAG CCATGAGCGT TCATTTCACA      60

TTCATTTGAA AA      72

(2) INFORMATION FOR SEQ ID NO: 10:

(i) SEQUENCE CHARACTERISTICS:
      (A) LENGTH: 60 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 10:

CCAAACTCCA TCAACAGTCA GTAATACAGG ATCATAAACC ATTGGACACA TAACGTCTTC      60

(2) INFORMATION FOR SEQ ID NO: 11:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 11:

AGATCCAAGC TTTTCCGCAA TTATATCATT                                              30

(2) INFORMATION FOR SEQ ID NO: 12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

GGATTCAAGC TTTGCTCAGT TTTGCTTCTG                                              30

(2) INFORMATION FOR SEQ ID NO: 13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

AAGCTTCAGG ATGTTCATAA TTTTTAAAGA TC                                           32

(2) INFORMATION FOR SEQ ID NO: 14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

GCCCAGGCGG CAGGGGAATT CAAATCAAAC GGGGAA                                       36

(2) INFORMATION FOR SEQ ID NO: 15:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

GCGGCAGCTC AGTAAGGATC CAACATAAAA AACCGGC                                      37

(2) INFORMATION FOR SEQ ID NO: 16:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

GAAGACGTTA TGTGTCCGGA TGTTTATGAT CCTGTA                                       36

(2) INFORMATION FOR SEQ ID NO: 17:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

```
GTATTACTGA CTGTTTGTGG AGTTTGGCAA GGTAAACGTG TATCTTATGA ACGT        54
```

(2) INFORMATION FOR SEQ ID NO: 18:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

```
GAAGACGTTA TGTGTCCCCC GGTTTATGAT CCTGTA                            36
```

(2) INFORMATION FOR SEQ ID NO: 19:

(i) SEQUENCE CHARACTERISTICS:
        (A) LENGTH: 342 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

```
GATG CTCCTTCTGC ACTTTATGCA CCTTCAGCAT TAGTTTTAAC AGTTGGTAAA        54
GGAGTTAGCG CTACGACAGC TGCACCTGAA AGAGCAGTAA CTCTTACATG TGCTCCAGGC  114
CCTTCTGGTA CACATCCAGC AGCTGGCTCT GCATGTGCAG ATTTAGCTGC AGTAGGAGGT  174
GACTTAAACG CATTAACACG TGGTGAAGAC GTTATGTGTC AATGGTTTA TGATCCTGTA   234
TTACTGACTG TTGATGGAGT TTGGCAAGGT AAACGCGTAT CTTATGAACG TGTATTTTCA  294
AATGAATGTG AAATGAACGC TCATGGCTCT TCTGTATTTG CATTTTAA               342
```

(2) INFORMATION FOR SEQ ID NO: 20:

(i) SEQUENCE CHARACTERISTICS:
        (A) LENGTH: 113 amino acids
        (B) TYPE: amino acid
        (C) STRANDEDNESS: not relevant
        (D) TOPOLOGY: linear (ii) MOLECULE TYPE: protein (xi) SEQUENCE DESCRIPTION: SEQ ID NO: 20:

```
Asp Ala Pro Ser Ala Leu Tyr Ala Pro Ser Ala Leu
1               5                   10

Val Leu Thr Val Gly Lys Gly Val Ser Ala Thr Thr Ala Pro Gl
            15                  20                  25

Arg Ala Val Thr Leu Thr Cys Ala Pro Gly Pro Ser Gly Thr His Pr
        30                  35                  40

Ala Ala Gly Ser Ala Cys Ala Asp Leu Ala Ala Val Gly Gly Asp Le
```

```
                45                  50                  55                  60
Asn Ala Leu Thr Arg Gly Glu Asp Val Met Cys Pro Met Val Tyr As
                    65                  70                  75
Pro Val Leu Leu Thr Val Asp Gly Val Trp Gln Gly Lys Arg Val Se
                80                  85                  90
Tyr Glu Arg Val Phe Ser Asn Glu Cys Glu Met Asn Ala His Gly Se
            95                  100                 105
Ser Val Phe Ala Phe
        110
```